(12) United States Patent
Silver et al.

(10) Patent No.: US 10,806,490 B2
(45) Date of Patent: Oct. 20, 2020

(54) SINGLE LUMEN GAS SEALED ACCESS PORT FOR USE DURING ENDOSCOPIC SURGICAL PROCEDURES

(71) Applicant: Conmed Corporation, Utica, NY (US)

(72) Inventors: Mikiya Silver, New Haven, CT (US); Michael J. Kane, Clinton, CT (US); Michael J. Augelli, Prospect, CT (US)

(73) Assignee: Conmed Corporation, Utica, NY (US)

( * ) Notice: Subject to any disclaimer, the term of this patent is extended or adjusted under 35 U.S.C. 154(b) by 207 days.

(21) Appl. No.: 15/896,302

(22) Filed: Feb. 14, 2018

(65) Prior Publication Data

US 2018/0256205 A1   Sep. 13, 2018

Related U.S. Application Data

(60) Provisional application No. 62/468,417, filed on Mar. 8, 2017.

(51) Int. Cl.
*A61B 17/34*   (2006.01)
*A61M 13/00*   (2006.01)
(Continued)

(52) U.S. Cl.
CPC ...... *A61B 17/3423* (2013.01); *A61B 17/3421* (2013.01); *A61B 17/3462* (2013.01); *A61B 17/3474* (2013.01); *A61B 17/3498* (2013.01); *A61M 1/0023* (2013.01); *A61M 13/006* (2014.02); *A61B 2017/00477* (2013.01); *A61B 2017/3419* (2013.01); *A61B 2017/3445* (2013.01); *A61B 2218/006* (2013.01); *A61M 16/0858* (2014.02); *A61M 2202/0007* (2013.01); *A61M 2202/0014* (2013.01);
(Continued)

(58) Field of Classification Search
CPC ............ A61B 17/3423; A61B 17/3474; A61B 2017/00477; A61M 1/0023; A61M 13/006; A61M 2202/0014; A61M 16/0858; A61M 2205/75; A61M 2205/3344
See application file for complete search history.

(56) References Cited

U.S. PATENT DOCUMENTS 6,811,546 B1   11/2004 Callas et al.
7,182,752 B2   2/2007 Stubbs et al.
(Continued)

OTHER PUBLICATIONS

International Search Report issued in corresponding PCT Patent Application No. PCT/US2018/019495, dated Jun. 8, 2018.

*Primary Examiner* — Bradley J Osinski
(74) *Attorney, Agent, or Firm* — Locke Lord LLP; Scott D. Wofsy

(57) ABSTRACT

A system for performing an endoscopic surgical procedure in a surgical cavity of a patient that includes a multi-lumen tube set including a dual lumen portion having a pressurized gas line and a return gas line for facilitating gas recirculation relative to the surgical cavity of the patient, and a single lumen portion having a gas supply and sensing line for delivering insufflation gas to the surgical cavity of the patient and for periodically sensing pressure within the surgical cavity of the patient, a first gas sealed single lumen access port communicating with the dual lumen portion of the tube set and a second valve sealed single lumen access port communicating with the single lumen portion of the tube set.

6 Claims, 20 Drawing Sheets

(51) Int. Cl.
*A61M 1/00* (2006.01)
*A61B 17/00* (2006.01)
*A61M 16/08* (2006.01)

(52) U.S. Cl.
CPC .............. *A61M 2202/0225* (2013.01); *A61M 2205/3344* (2013.01); *A61M 2205/75* (2013.01)

(56) References Cited

U.S. PATENT DOCUMENTS

| | | | |
|---|---|---|---|
| 7,285,112 B2 | 10/2007 | Stubbs et al. | |
| 7,338,473 B2 * | 3/2008 | Campbell | A61B 17/3421 604/164.01 |
| 7,413,559 B2 | 8/2008 | Stubbs et al. | |
| 7,854,724 B2 | 12/2010 | Stearns et al. | |
| 7,976,598 B2 | 7/2011 | Matula et al. | |
| 8,088,189 B2 | 1/2012 | Matula et al. | |
| 8,216,189 B2 | 7/2012 | Stubbs et al. | |
| 8,641,608 B2 | 2/2014 | Voegele et al. | |
| 8,715,219 B2 | 5/2014 | Stearns et al. | |
| RE44,972 E | 7/2014 | Matula et al. | |
| 8,795,223 B2 * | 8/2014 | Stearns | A61B 17/3462 604/26 |
| 8,961,451 B2 | 2/2015 | Stearns et al. | |
| 9,067,030 B2 | 6/2015 | Stearns et al. | |
| D735,331 S | 7/2015 | Mastri et al. | |
| 9,095,372 B2 | 8/2015 | Stearns et al. | |
| 9,199,047 B2 | 12/2015 | Stearns et al. | |
| 9,295,490 B2 | 3/2016 | Stearns et al. | |
| 9,375,539 B2 | 6/2016 | Stearns et al. | |
| 9,387,296 B1 | 7/2016 | Mastri et al. | |
| 9,414,818 B2 | 8/2016 | Azarbarzin et al. | |
| 9,526,849 B2 | 12/2016 | Stearns et al. | |
| 9,526,886 B2 | 12/2016 | Mastri et al. | |
| 9,545,264 B2 | 1/2017 | Mastri et al. | |
| 2007/0088275 A1 | 4/2007 | Stearns et al. | |
| 2009/0234193 A1 | 9/2009 | Weisenburgh, II et al. | |
| 2014/0171855 A1 * | 6/2014 | Mastri | A61M 39/1011 604/26 |
| 2017/0050011 A1 | 2/2017 | Zergiebel et al. | |

* cited by examiner

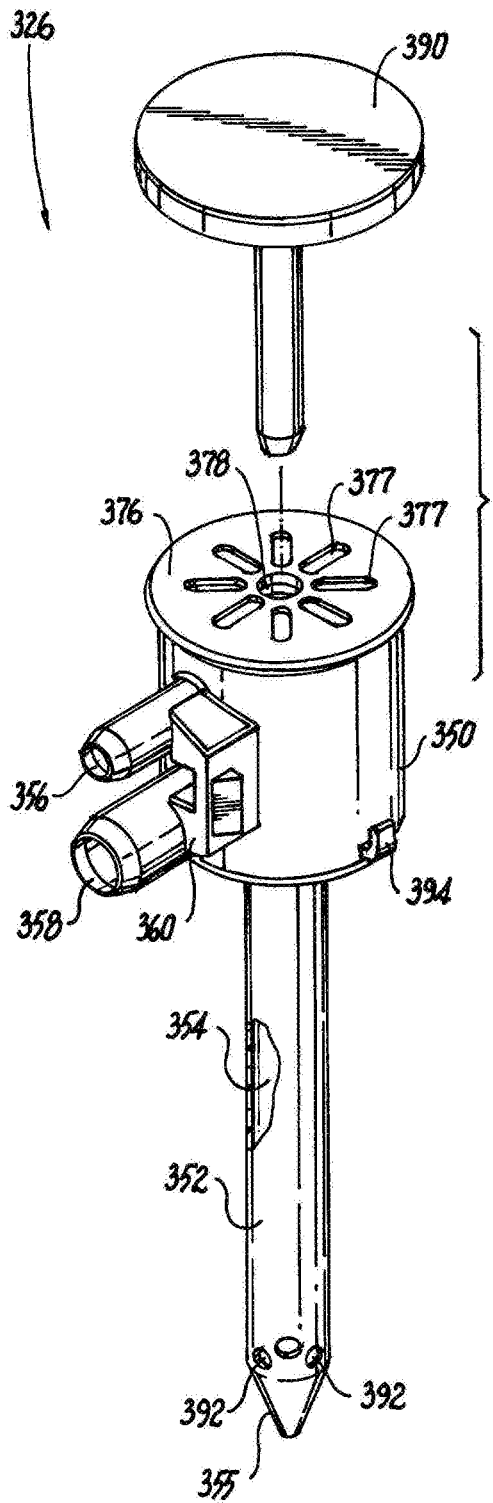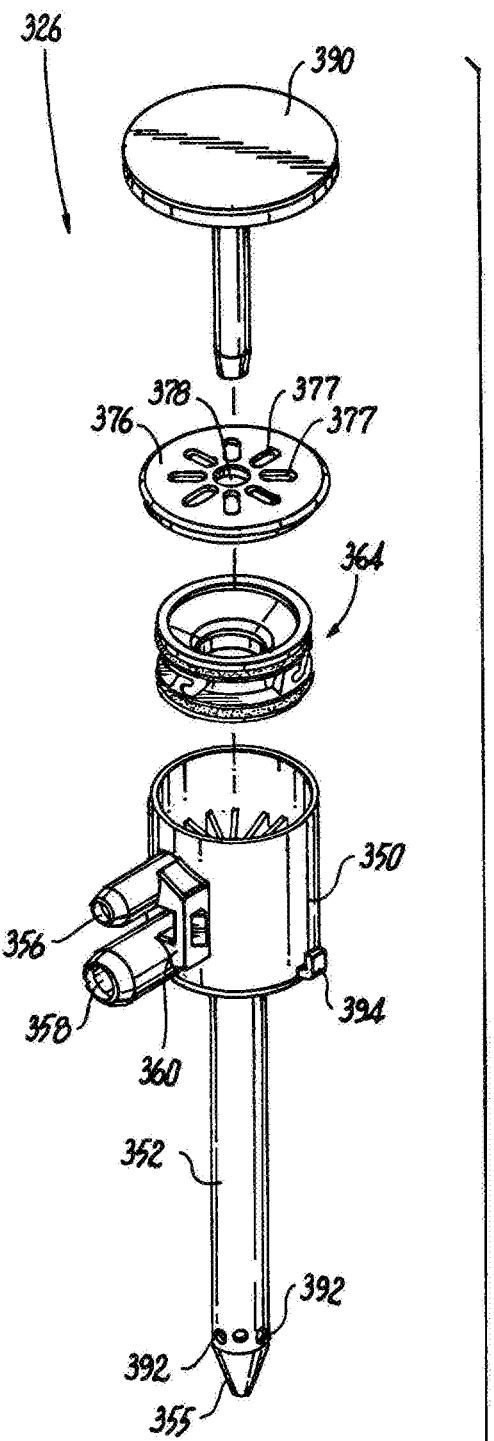
Fig. 14   Fig. 15

SINGLE LUMEN GAS SEALED ACCESS PORT FOR USE DURING ENDOSCOPIC SURGICAL PROCEDURES

CROSS-REFERENCE TO RELATED APPLICATION

This application claims the benefit of priority to U.S. Provisional Patent Application Ser. No. 62/468,417 filed Mar. 8, 2017, the disclosure of which is herein incorporated by reference in its entirety.

BACKGROUND OF THE INVENTION

1. Field of the Invention

The subject invention is directed to endoscopic surgery, and more particularly, to a surgical gas circulation system with multi-lumen tube set connected with a single lumen gas sealed access port and a single lumen valve sealed access port for use during an endoscopic or laparoscopic surgical procedure.

2. Description of Related Art

Laparoscopic or "minimally invasive" surgical techniques are becoming commonplace in the performance of procedures such as cholecystectomies, appendectomies, hernia repair and nephrectomies. Benefits of such procedures include reduced trauma to the patient, reduced opportunity for infection, and decreased recovery time. Such procedures within the abdominal (peritoneal) cavity are typically performed through a device known as a trocar or cannula, which facilitates the introduction of laparoscopic instruments into the abdominal cavity of a patient.

Additionally, such procedures commonly involve filling or "insufflating" the abdominal cavity with a pressurized fluid, such as carbon dioxide, to create an operating space, which is referred to as a pneumoperitoneum. The insufflation can be carried out by a surgical access device, such as a trocar, equipped to deliver insufflation fluid, or by a separate insufflation device, such as an insufflation (veress) needle. Introduction of surgical instruments into the pneumoperitoneum without a substantial loss of insufflation gas is desirable, in order to maintain the pneumoperitoneum.

During typical laparoscopic procedures, a surgeon makes three to four small incisions, usually no larger than about twelve millimeters each, which are typically made with the surgical access devices themselves, often using a separate inserter or obturator placed therein. Following insertion, the obturator is removed, and the trocar allows access for instruments to be inserted into the abdominal cavity. Typical trocars provide a pathway to insufflate the abdominal cavity, so that the surgeon has an open interior space in which to work.

The trocar must also provide a way to maintain the pressure within the cavity by sealing between the trocar and the surgical instrument being used, while still allowing at least a minimum amount of freedom of movement for the surgical instruments. Such instruments can include, for example, scissors, grasping instruments, and occluding instruments, cauterizing units, cameras, light sources and other surgical instruments. Sealing elements or mechanisms are typically provided on trocars to prevent the escape of insufflation gas from the abdominal cavity. These sealing mechanisms often comprise a duckbill-type valve made of a relatively pliable material, to seal around an outer surface of surgical instruments passing through the trocar.

SurgiQuest, Inc., a wholly owned subsidiary of ConMed Corporation has developed unique gas sealed surgical access devices that permit ready access to an insufflated surgical cavity without the need for conventional mechanical valve seals, as described, for example, in U.S. Pat. No. 7,854,724. These devices are constructed from several nested components including an inner tubular body portion and a coaxial outer tubular body portion. The inner tubular body portion defines a central lumen for introducing conventional laparoscopic surgical instruments to the abdominal cavity of a patient and the outer tubular body portion defines an annular lumen surrounding the inner tubular body portion for delivering insufflation gas to the abdominal cavity of the patient and for facilitating periodic sensing of abdominal pressure.

While these earlier developed dual lumen gas sealed access devices provide significant benefits and improvements over conventional single lumen valve sealed access devices, they do present certain disadvantages in the performance of a laparoscopic surgical procedure. In particular, because these earlier developed dual lumen gas sealed access devices are constructed with two coaxial tubular body portions, the effective outer diameter of the tubular body of the access device is significantly greater than the effective outer diameter of the tubular body of a conventional single lumen valve sealed access device.

For example, the outer diameter of the dual lumen gas sealed access device may be at least 2.0 mm greater than the outer diameter of a conventional single lumen valve sealed access device. Consequently, the length of the incision that is required to introduce the dual lumen access device into the abdominal cavity will be greater than the typical incision that is made for introducing a conventional single lumen valve sealed access device. This larger incision can increase the degree of patient trauma, cause larger and more visible scars for the patient, more pain or pain medication, and more difficult wound closure for the surgeon.

It would be beneficial therefore to provide a gas sealed surgical access device that overcomes the disadvantages associated with earlier developed dual lumen gas sealed access devices, such as those disclosed in U.S. Pat. No. 7,854,724, while maintaining the substantial benefits they provide over conventional single lumen valve sealed access devices. The subject invention provides such a novel access device and a filtered tube set for the device for use in endoscopic surgery, which is described in detail herein below.

SUMMARY OF THE DISCLOSURE

The subject invention is directed to a new and useful system for performing an endoscopic or laparoscopic surgical procedure in a surgical cavity of a patient. The system includes a multi-lumen tube set including a dual lumen portion and a single lumen portion. The dual lumen portion of the tube set has a pressurized gas line and a return gas line, which together facilitate gas recirculation relative to the surgical cavity of the patient. The single lumen portion of the tube set has a gas supply and sensing line for delivering insufflation gas to the surgical cavity of the patient and for periodically sensing pressure within the surgical cavity of the patient. Preferably, the tube set is operatively associated with a multi-path filter cartridge assembly.

The system further includes a first access port having a proximal housing portion and an elongated tubular body portion extending distally from the proximal housing portion and defining a central cannula or bore. The proximal housing portion of the first access port has an inlet path for communicating with the pressurized gas line of the tube set and an outlet path for communicating with the return gas line of the tube set. The proximal housing portion accommodates an annular jet assembly for receiving pressurized gas from the inlet path and for generating a gaseous sealing zone within the central cannula of the body portion to maintain a stable pressure within the surgical cavity of the patient.

The system also includes a second access port having a proximal housing portion and a tubular body portion extending from the proximal housing portion. The proximal housing portion of the second access port accommodates a mechanical valve for sealing the tubular body portion and an inlet path for communicating with the gas supply and sensing line of the tube set.

Preferably, the first access port is adapted and configured to perform smoke evacuation from the surgical cavity of the patient in conjunction with the second access port. In one embodiment of the invention, the first access port is adapted and configured to permit air entrainment, emergency relief of cavity pressure and instrument access into the central cannula during a surgical procedure. In another embodiment of the invention, the first access port is adapted and configured to permit air entrainment and emergency relief of cavity pressure, but without permitting instrument access into and/or through the central cannula. In this regard, the central bore of the cannula may be shaped, dimensioned, louvered or otherwise configured to prevent instrument access therethrough.

In another embodiment, the first access port includes a proximal housing portion that is adapted to be selectively coupled with the tubular body portion thereof, and wherein the tubular body portion is configured for manipulation by a robotic surgical system, such as, for example, Da Vinci robotic system manufactured by Intuitive Surgical, Inc. For example, the proximal housing portion may be selectively coupled to the tubular body portion by a pair of diametrically opposed cantilevered or spring loaded locking tabs or the like. The locking tabs can be provided on the proximal housing portion or on the tubular body portion. The tubular body portion would include a grasping flange for enabling a robotic manipulator to grasp and move the abdominal port during a surgical procedure.

Alternatively, in this embodiment, the first access port includes a proximal housing portion that is adapted to be selectively coupled with the tubular body portion thereof, wherein the tubular body portion is of a proprietary design, or wherein the tubular body portion is of a non-proprietary design.

In accordance with a preferred embodiment of the subject invention, the proximal housing portion includes a manifold defining the gas inlet path and the gas outlet path for the access port. Preferably, the inlet and outlet paths are concentrically arranged within the manifold, and the dual lumen portion of the tube set includes a coaxial connector for coupling with the manifold. Alternatively, the inlet and outlet paths are arranged in parallel within the manifold, and the dual lumen portion of the tube set includes a suitable connector for coupling with the manifold. In comparison, the single lumen portion of the tube set can include a luer type connector for coupling with a conventional luer type fitting associated with the inlet path of the second access port.

The system further includes a gas recirculation apparatus including a pump having an outlet for delivering pressurized gas to the tube set and an inlet for receiving depressurized gas from the return line of the tube set through the filter cartridge assembly. The apparatus is also configured to deliver insufflation gas to the gas supply and sensing line of the tube set from a gas source, as disclosed, for example, in commonly assigned U.S. Pat. No. 9,375,539. In accordance with a preferred embodiment of the subject invention, the gas recirculation apparatus may include a programmable controller with software that is adapted and configured to detect the presence of the bifurcated multi-lumen tube set and is able to differentiate it from a different type tube set.

The subject invention is also directed to a new and useful surgical access port for performing an endoscopic surgical procedure in a surgical cavity of a patient, which includes a proximal housing portion and an elongated tubular body portion extending distally from the proximal housing portion and defining a central cannula or bore. The proximal housing portion has an inlet path for communicating with a pressurized gas line of a tube set and an outlet path for communicating with a return gas line of the tube set. The proximal housing portion accommodates an annular jet assembly for receiving pressurized gas from the inlet path and for generating a gaseous sealing zone within the central cannula of the body portion to maintain a stable pressure within the surgical cavity of the patient.

The subject invention is also directed to new and useful multi-lumen tube set for performing an endoscopic surgical procedure in a surgical cavity of a patient, which includes a multi-path filter cartridge assembly, a dual lumen portion communicating with the filter cartridge assembly and having a pressurized gas line and a return gas line for facilitating gas recirculation relative to the surgical cavity of the patient, and a single lumen portion communicating with the filter cartridge assembly and having a gas supply and sensing line for delivering insufflation gas to the surgical cavity of the patient and for periodically sensing pressure within the surgical cavity of the patient. Preferably, the dual lumen portion of the tube set includes a unique coaxial connector, and the single lumen portion of the tube set can include a conventional luer type connector.

The subject invention is also directed to a novel method of retrofitting a separable two-part valve sealed surgical access port to perform an endoscopic surgical procedure in a surgical cavity of a patient. The method includes the step of obtaining a separable two-part surgical access port having a valve sealed proximal housing portion that is detachably engaged to a single lumen tubular body portion.

The method further includes the steps of detaching the valve sealed proximal housing portion from the single lumen tubular body portion and then attaching a gas sealed proximal housing portion to the single lumen tubular body portion, wherein the tubular body portion may be configured for manipulation by a robotic surgical system. The method further includes the step of connecting the gas sealed proximal housing portion to a source of pressurized gas for generating a gaseous sealing zone within a central cannula of the single lumen tubular body portion to maintain a stable pressure within the surgical cavity of the patient.

The subject invention is also directed to a method of retrofitting a reusable portion of a separable two-part valve sealed surgical access port to perform an endoscopic surgical procedure in a surgical cavity of a patient. The method includes the step of obtaining a reusable portion of a surgical access port normally having a valve sealed proximal housing portion that is detachably engaged to a reusable single lumen tubular body portion.

The method further includes the steps of attaching a gas sealed proximal housing portion to the reusable single lumen tubular body portion, wherein the reusable tubular body portion may be configured for manipulation by a robotic surgical system. The method further includes the step of connecting the gas sealed proximal housing portion to a source of pressurized gas for generating a gaseous sealing zone within a central cannula of the reusable single lumen tubular body portion to maintain a stable pressure within the surgical cavity of the patient.

These and other features of the gas circulation system and the single lumen gas sealed access device of the subject invention will become more readily apparent to those having ordinary skill in the art to which the subject invention appertains from the detailed description of the preferred embodiments taken in conjunction with the following brief description of the drawings.

BRIEF DESCRIPTION OF THE DRAWINGS

So that those skilled in the art will readily understand how to make and use the gas circulation system and gas sealed abdominal access devices of the subject invention without undue experimentation, preferred embodiments thereof will be described in detail herein below with reference to the figures wherein:

FIG. 14 is a perspective view of another embodiment of a single lumen gas sealed trocar constructed in accordance with the subject invention which is configured for air entrainment and emergency pressure relief, without permitting instrument access through the central bore of the cannula, wherein the trocar includes a closed obturator tip to prevent passage of an instrument through the cannula into the surgical cavity;

FIG. 15 is an exploded perspective view of the gas sealed trocar of FIG. 14, with parts separated for ease of illustration;

FIGS. 35-38 illustrate the method steps involved in retrofitting a separable two-part valve sealed access port to perform an endoscopic surgical procedure in a surgical cavity of a patient, wherein:

FIG. 35 shows a separable two-part access port having a valve sealed proximal housing portion that is detachably engaged to a single lumen tubular body portion;

FIG. 36 shows detaching the valve sealed proximal housing portion from the single lumen tubular body portion of the access port;

FIG. 37 shows attaching a gas sealed proximal housing portion to the single lumen tubular body portion of the access port; and FIG. 38 shows the fully assembled single lumen gas sealed access port, as illustrated in FIG. 32.

DETAILED DESCRIPTION OF THE PREFERRED EMBODIMENTS

Figure 1:
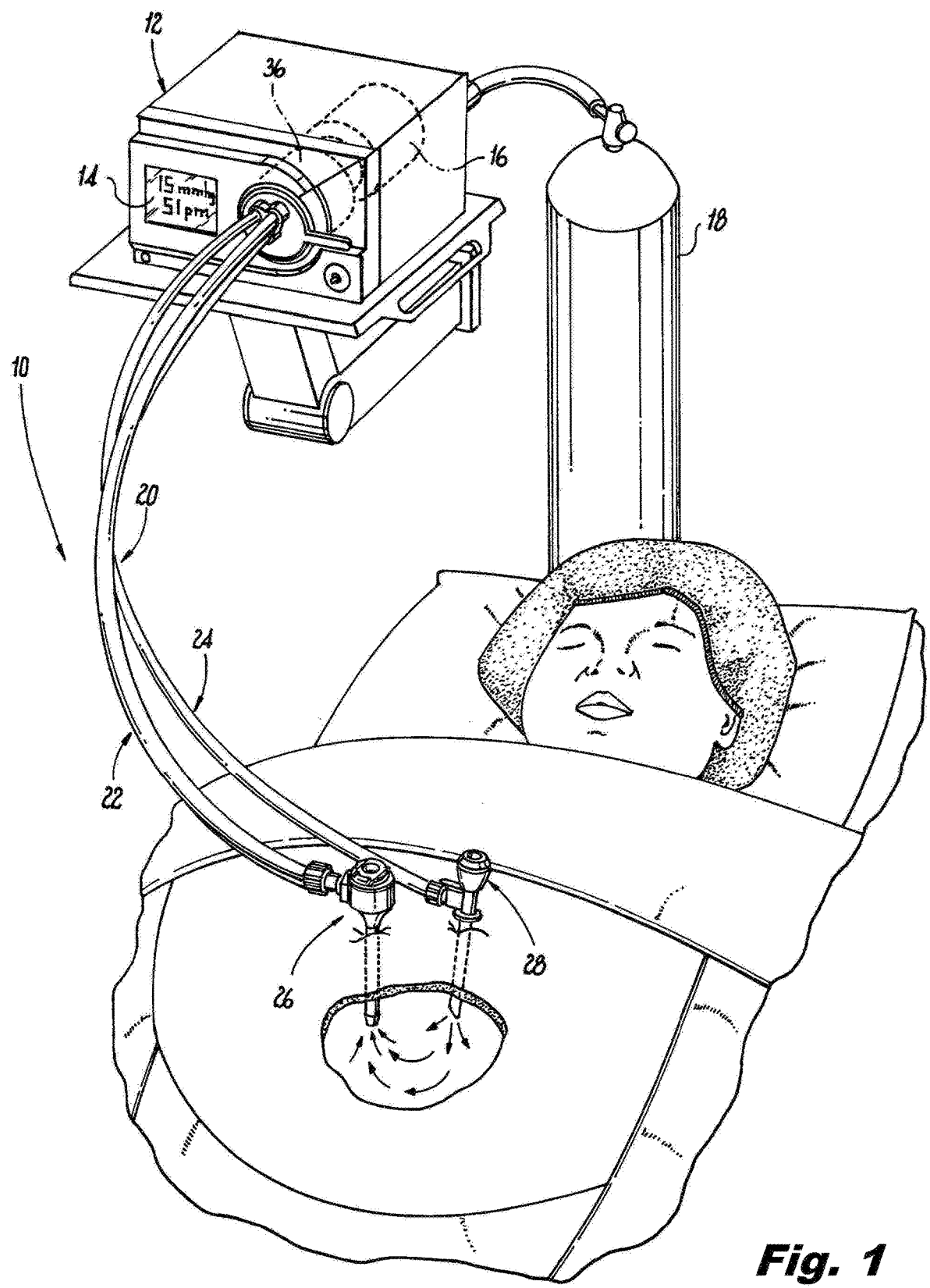
FIG. 1 is a perspective view of the gas circulation system of the subject invention in use during the performance of a laparoscopic surgical procedure, wherein the gas circulation system includes a multi-lumen filtered tube set having a dual lumen portion connected to a single lumen gas sealed access port configured for maintaining a stable pneumoperitoneum within the abdominal cavity of the patient and for facilitating smoke evacuation from the abdominal cavity, and a single lumen portion connected to a single lumen valve sealed access port configured for insufflation and abdominal pressure sensing.

Referring now to the drawings wherein like reference numerals identify similar structural elements and features of the subject invention, there is illustrated in FIG. 1 a gas circulation system for performing an endoscopic surgical procedure in a surgical cavity of a patient, and more particularly, for performing a laparoscopic surgical procedure in the abdominal cavity of a patient that is constructed in accordance with a preferred embodiment of the subject disclosure and is designated generally by reference numeral 10.

The gas circulation system 10 is specifically designed to cooperate with a programmable multi-modal gas delivery system 12. The gas delivery system 12 is of the type described in commonly assigned U.S. Pat. No. 9,375,539, the disclosure of which is herein incorporated by reference in its entirety. The gas delivery system 12 includes a graphical user interface 14 for setting operating parameters and a pump 16 for facilitating the recirculation of pressurized gas relative to the surgical cavity of the patient. The gas delivery system 12 is connected to a source of surgical gas 18 for delivering insufflation gas to the surgical cavity of the patient.

In brief, the gas circulation system 10 includes a multi-lumen filtered tube set 20 including a dual lumen portion 22 and a single lumen portion 24, a first gas sealed single lumen access port 26 operatively connected to the dual lumen portion 22 of the tube set 20 and a second valve sealed single lumen access port 28 operatively connected to the single lumen portion 24 of the tube set 20. Each of these components of the gas circulation system 10, and variations thereof, will be described in greater detail herein below.

The Multi-Lumen Tube Set

Figure 2:
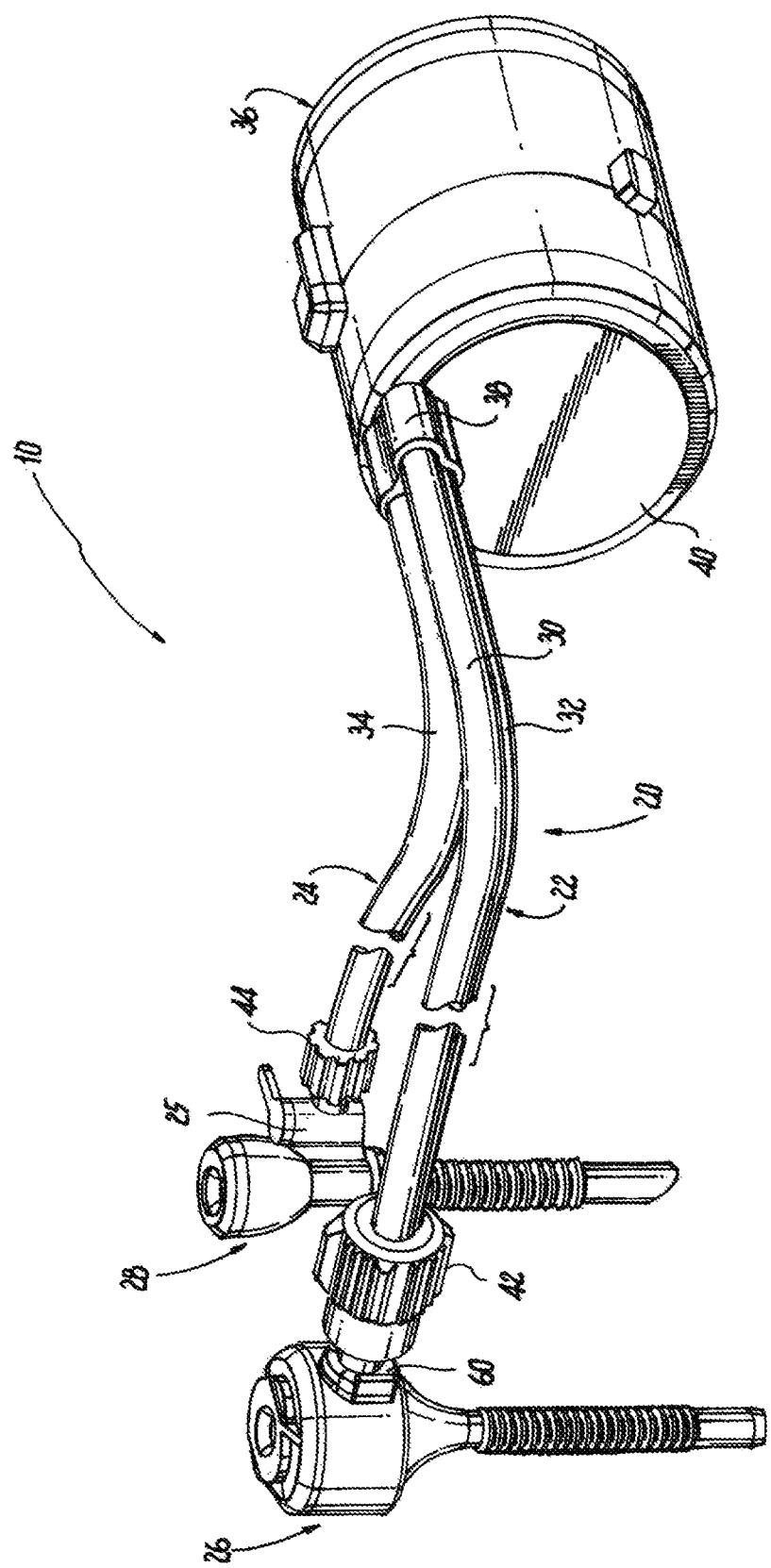
FIG. 2 is a perspective view of the gas circulation system shown in FIG. 1, including a filter cartridge assembly, and a multi-lumen filtered tube set having a dual lumen portion connected to a single lumen gas sealed access port and a single lumen portion connected to a single lumen valve sealed access port.
Figure 3:
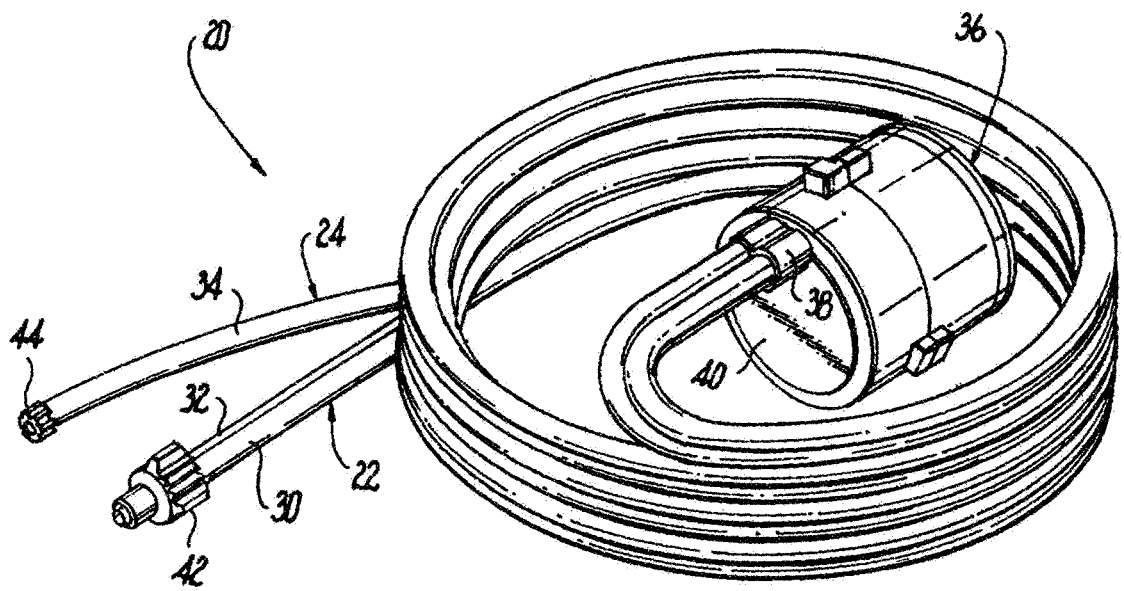
FIG. 3 is a perspective view of the multi-lumen filtered tube set of the subject invention, wherein a conventional luer connector is associated with the single lumen portion of the tube set and a dual lumen connector with concentric flow passages is associated with the dual lumen portion of the tube set.
Figure 4:
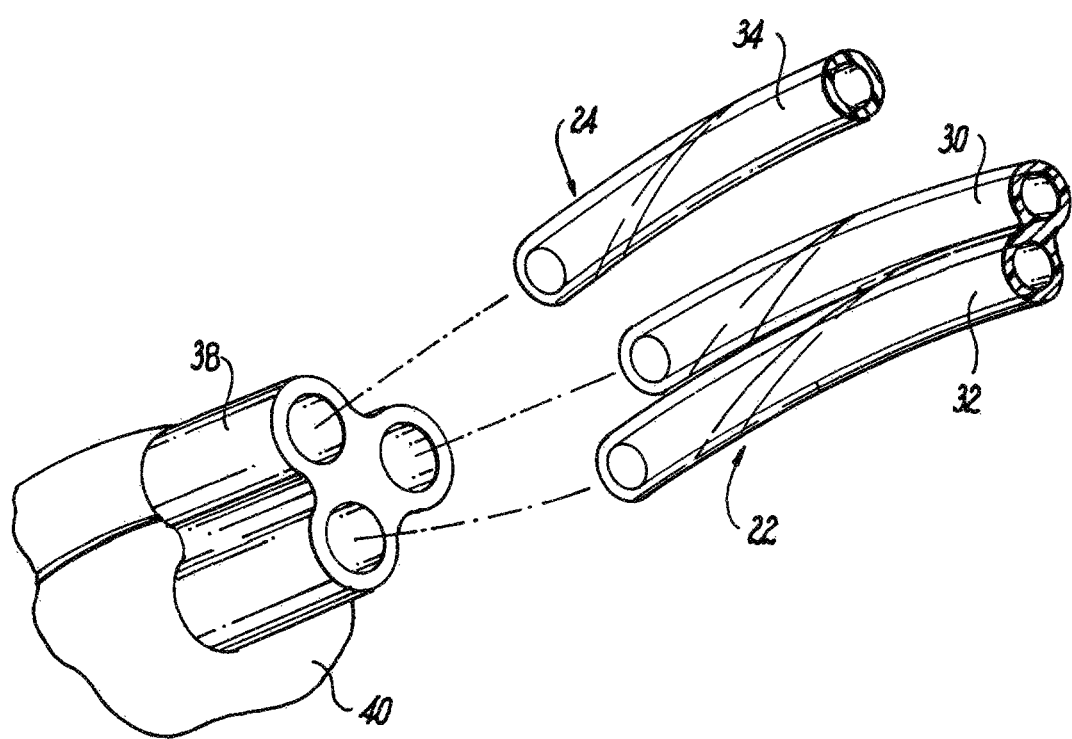
FIG. 4 is an enlarged localized perspective view of the tube fitting on the filter cartridge assembly shown in FIG. 3, with parts separated for ease of illustration.

Referring to FIGS. 2-4, the gas circulation system 10 of the subject invention includes a multi-lumen filtered tube set designated generally by reference numeral 20 that includes a dual lumen portion 22 and a single lumen portion 24. The dual lumen portion 22 has a pressurized gas line 30 and a return gas line 32 for facilitating gas recirculation relative to the surgical cavity of the patient. The single lumen portion 24 has a gas supply and sensing line 34 for delivering insufflation gas to the surgical cavity of the patient and for periodically sensing pressure within the surgical cavity of the patient.

The tube set 20 is operatively associated with a multi-path filter cartridge assembly 36. More particularly, the gas lines of the tube set 20 extend from a fitting 38 on the end cap 40 of the filter cartridge assembly 36. A filter cartridge assembly of this type is disclosed for example in commonly assigned U.S. Pat. No. 9,067,030 the disclosure of which is herein incorporated by reference in its entirety. The filter cartridge assembly 36 is preferably designed for a single use and is thereafter disposable. It is specifically designed to cooperate with the multi-modal gas delivery system 12, illustrated in FIG. 1 and described in commonly assigned U.S. Pat. No. 9,375,539.

While not shown here, the filter cartridge assembly 36 includes a first filtered flow passage communicating with the pressurized gas line 30 of the dual lumen portion 22 of the tube set 20, a second filtered flow passage communicating with the return gas line 32 of the dual lumen portion 22 of the tube set 20, and a third filtered flow passage communicating with the gas supply and sensing line 34 of the single lumen portion 24 of the tube set 20.

Figure 3A:
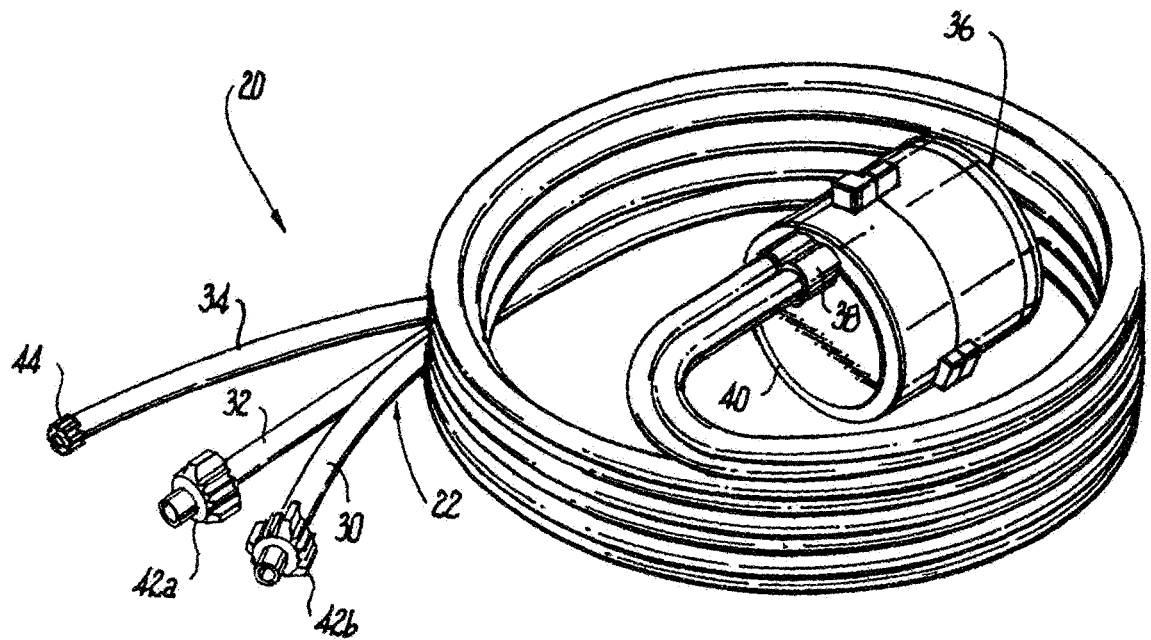
FIG. 3A is a perspective view on another multi-lumen tube set of the subject invention, wherein the dual lumen portion is bifurcated and each of the tubes has a separate connector.

As shown in FIGS. 2, 3 and 3A, the single lumen portion 24 of the tube set 20 includes a standard luer type connector 44 for connecting to a luer connection 25 on the valve sealed access port 28. The dual lumen portion 22 of the tube set 20 includes a dual lumen manifold connector 42 with coaxial flow passages for mating with a dual lumen manifold connector 60 on gas sealed access portion 26. In a preferred embodiment of the subject invention, the dual lumen portion 22 of the tube set 20 is at least partially formed as a conjoined extrusion, as best seen in FIG. 4. Alternatively, as shown in FIG. 3A, the dual lumen portion 22 of tube set 20 can be distally bifurcated into two separated gas lines 30 and 32, each with a single connector for mating with a correspondingly configured access port manifold, as shown for example in FIG. 14.

Single Lumen Gas Sealed Access Port

With continuing reference to FIGS. 1 and 2 in conjunction with FIGS. 5-9, the circulation system 10 includes a gas sealed single lumen access port 26 that is adapted and configured to provide gas sealed access to the surgical cavity of a patient during an endoscopic surgical procedure. In this regard, access port 26 functions similar to the dual-lumen trocar assembly that is disclosed, for example, in commonly assigned U.S. Pat. No. 7,854,724, the disclosure of which is herein incorporated by reference in its entirety. However, access port 26 differs significantly from the trocar assembly disclosed in U.S. Pat. No. 7,854,724 in that it has only one central lumen.

Figure 9:
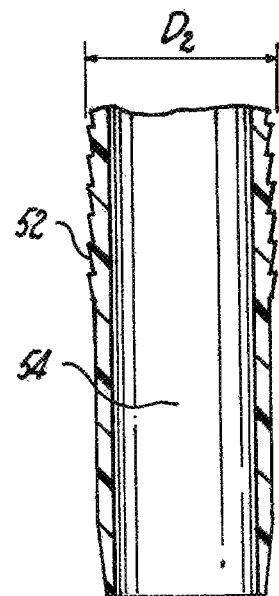
FIG. 9 is an enlarged localized view of the distal end portion of the single lumen gas sealed access port of FIG. 5, which has an outer diameter $D_2$.
Figure 10:
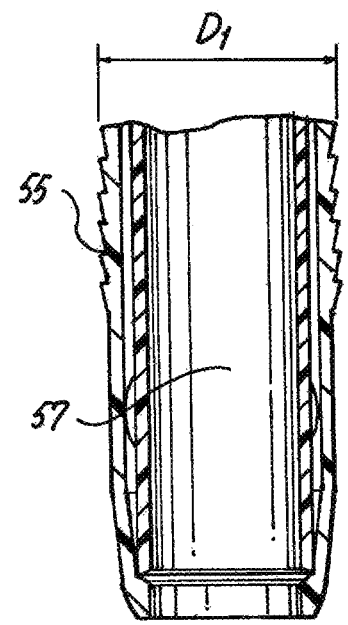
FIG. 10 is an enlarged localized view of the distal end portion of a prior art dual lumen gas sealed access port, which has an outer diameter $D_1$.

The access port 26 of the subject invention does not have a second annular lumen surrounding the central lumen, as shown for example in the prior art FIG. 10. Thus, access port 26 is not capable of delivering insufflation gas to the surgical cavity of a patient, nor is it capable of sensing cavity pressure. Rather, access port 26 is configured to provide gas sealed instrument access while facilitating the maintenance of stable cavity pressure and smoke evacuation from the surgical cavity. The access port 26 will be described in greater detail below with regard to FIGS. 5 through 9.

Referring now to FIGS. 5 through 9, there is illustrated in more detail the single lumen gas sealed access port 26 of the subject invention, which includes a proximal housing portion 50 and an elongated tubular body portion 52 extending distally from the proximal housing portion 50 and defining a central cannula 54. The proximal housing portion 50 of access port 26 has an inlet path 56 for communicating with the pressurized gas line 30 of the tube set 20 and an outlet path 58 for communicating with the return gas line 32 of the tube set 20.

Figure 5:
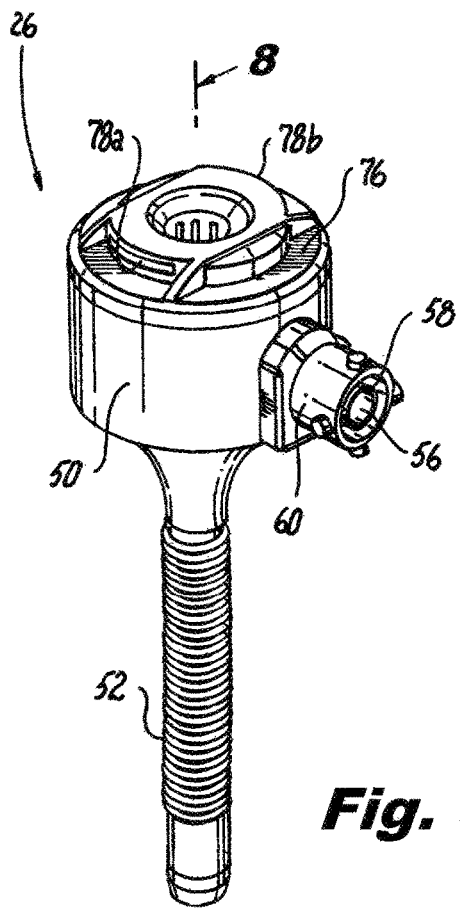
FIG. 5 is a perspective view of a single lumen gas sealed access port constructed in accordance with a preferred embodiment of the subject invention.
Figure 5A:
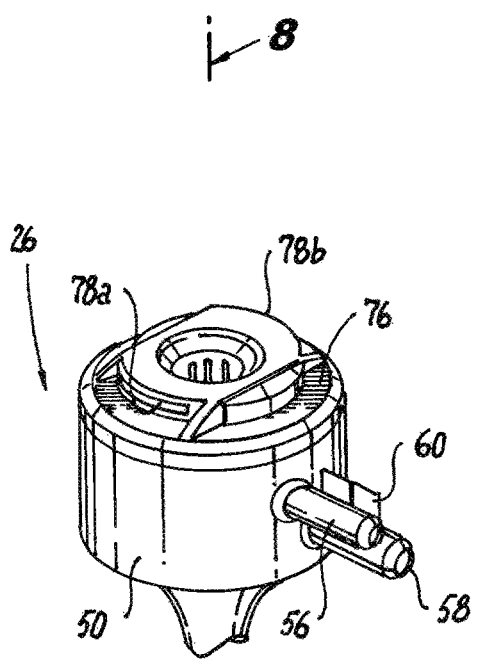
FIG. 5A is a perspective view of the housing portion of a single lumen gas sealed access port similar to the embodiment of FIG. 5, but with a different manifold arrangement of the inlet and outlet paths.
Figure 8:
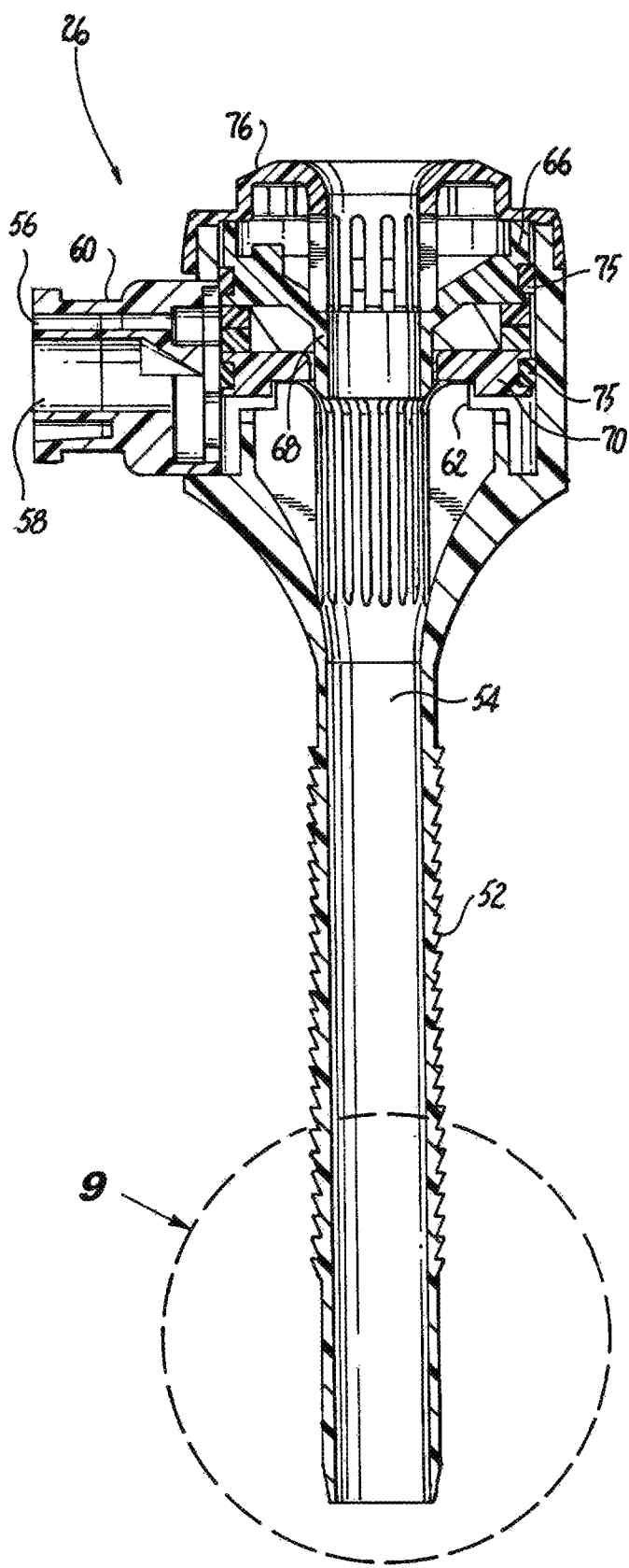
FIG. 8 is a cross-sectional view of the single lumen gas sealed access port, taken along line 8-8 of FIG. 5, illustrating the interior of the proximal housing portion that accommodates an annular jet assembly shown in FIG. 7, which generates a gaseous sealing zone within the central bore of the cannula to maintain stable pressure within the surgical cavity of a patient.

More particularly, as best seen in FIGS. 5 and 8, to manage gas flow in the access port 26, the proximal housing portion 50 includes a manifold 60 defining the inlet path 56 and the outlet path 58 which are concentrically arranged within the manifold 60. The dual lumen portion 22 of the tube set 20 includes the coaxial connector 42 for coupling with the manifold 60 of the proximal housing portion 50, as best seen in FIG. 2. A dual lumen coupled connection of this type is disclosed, for example, in FIG. 21 of commonly assigned U.S. Patent Application Publication 2017/0361084, the disclosure of which is incorporated herein by reference in its entirety. Alternatively, the single lumen gas sealed access port 26 could have a manifold 60 with two independent parallel connectors 56 and 58, as shown in FIG. 5A.

Figure 6:
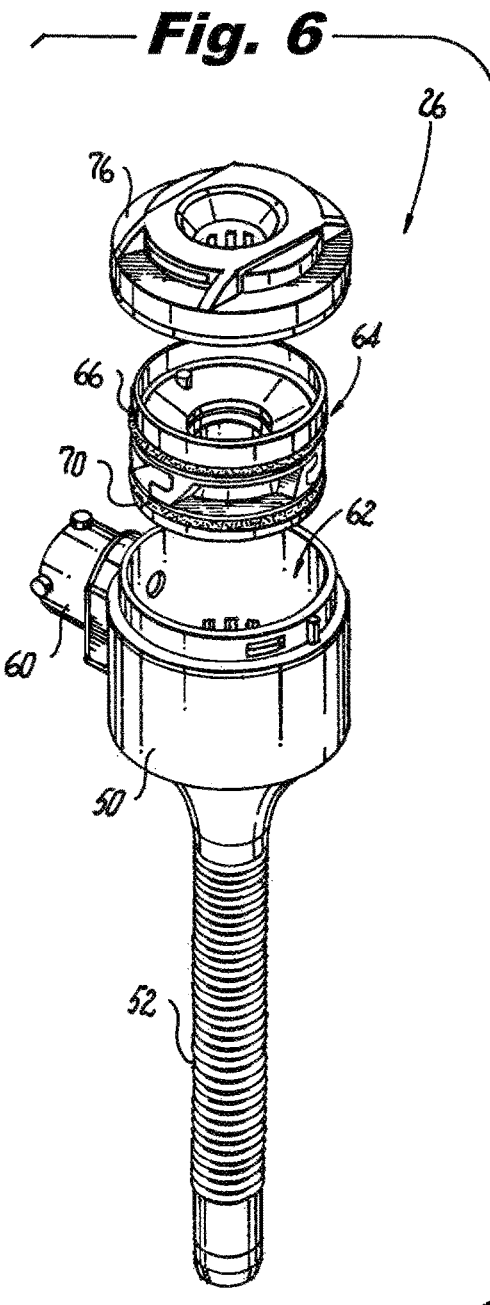
FIG. 6 is an exploded perspective view the single lumen gas sealed access port shown in FIG. 5, with parts separated for ease of illustration.
Figure 7:
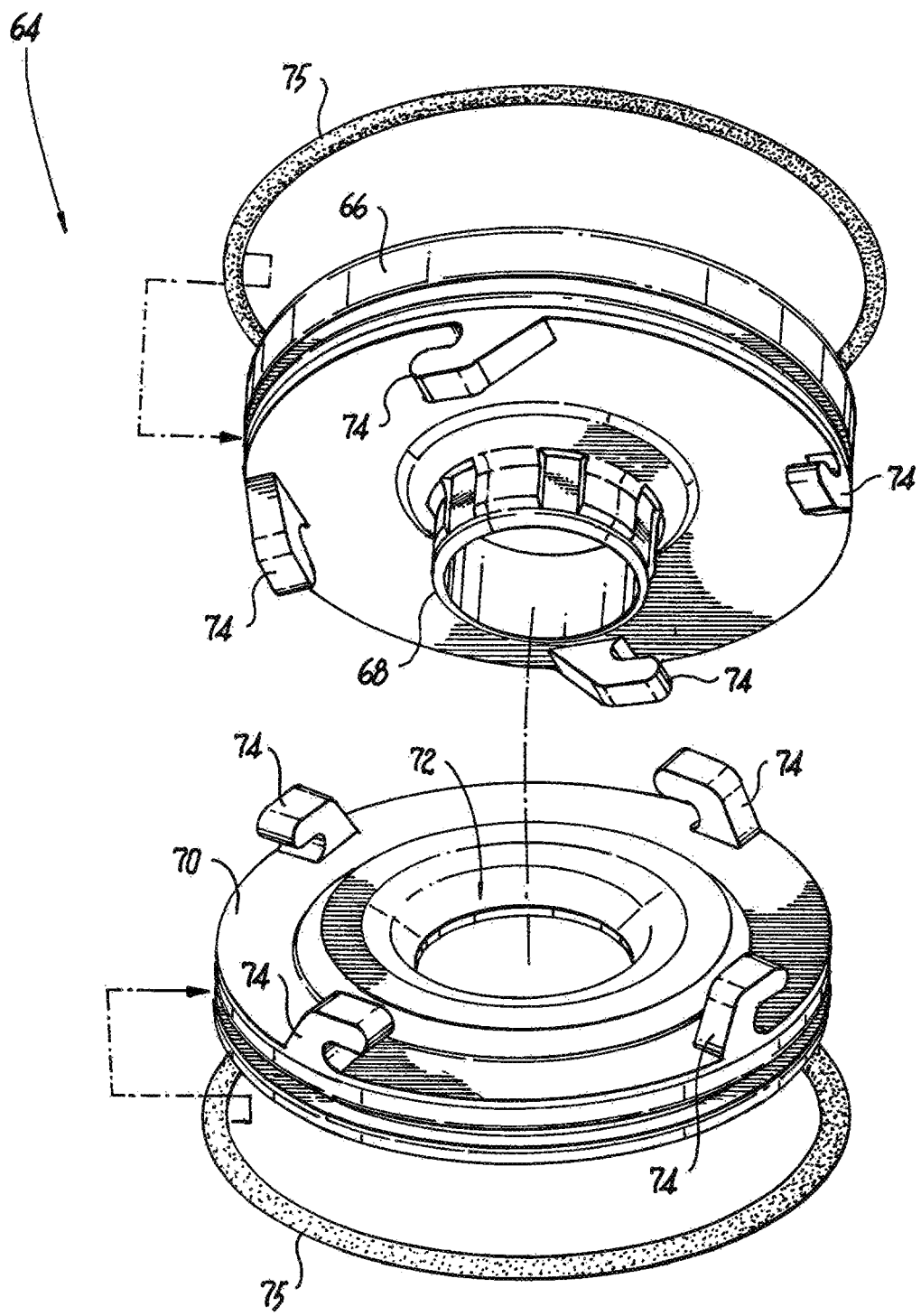
FIG. 7 is a perspective view of the annular jet assembly shown in FIG. 6, with parts separated for ease of illustration.

Referring to FIGS. 6 and 8, the proximal housing portion 50 of access port 26 defines an interior chamber 62 to accommodate a two-part annular jet assembly 64, which is best seen in FIG. 7. An end cap 76 covers the interior chamber 62 and defines an entry path for the central cannula 54. The annular jet assembly 64 is adapted and configured to receive pressurized gas from the inlet path 56 and for generating a gaseous or pneumatic sealing zone within the central cannula 54 of the tubular body portion 52 to maintain a stable pressure within the surgical cavity of the patient.

Referring to FIG. 7, the annular jet assembly 64 includes an upper jet ring 66 having a nozzle tube 68 and a lower jet ring 70 defining a nozzle seat 72 for receiving the nozzle tube 68. The upper jet ring 66 and lower jet ring 70 each has an O-ring 75 and they are joined together by a plurality of interfitting lugs 74. The annular jet assembly 64 is disclosed in great detail in commonly assigned U.S. Pat. No. 8,795,223 and U.S. Patent Application Publication 2015/0025323, the disclosures of which are herein incorporated by reference in their entireties.

There are several advantages to employing the gas circulation system 10 of the subject invention as compared to a system that utilizes the gas sealed access port disclosed for example in U.S. Pat. No. 8,795,223. In particular, with respect to the access port 26, by removing the need for both an inner and outer cannula, because of the use of a separate conventional cannula for insufflation and sensing, there is a significant reduction in the effective outer diameter of the tubular body of the access port 26.

FIGS. 9 and 10 illustrate this comparison, wherein FIG. 10 shows the tubular body portion 55 and central bore 57 of a 5 mm dual lumen gas sealed access device constructed in accordance with the disclosure of U.S. Pat. No. 8,795,223, which has an effective outer diameter $D_1$ of about 11.05 mm, whereas FIG. 9 shows a 5 mm version of the single lumen gas sealed access device 26 of the subject invention, which has a tubular body portion 52 with an effective outer diameter $D_2$, for example, of about 8.97 mm. It should be understood that the respective central bores 54, 57 of body portions 52, 55 have the same inner diameters.

This significant difference in the effective outer diameter of the single lumen gas sealed access port 26 of the subject invention enables surgery with a smaller patient incision, while maintaining similar functionality (i.e., gaseous sealing for instrumentation, stable pneumoperitoneum and smoke evacuation). A smaller incision size can also lead to smaller or invisible scars for the patient, less pain or pain medication, easier wound closure for the surgeon, etc. In addition, the single lumen gas sealed access port 26 of the subject invention uses less plastic and has fewer components than the gaseous sealed access port disclosed for example in U.S. Pat. No. 8,795,223, and the single lumen design eliminates several mating features. This could allow for lower component and assembly costs, as well as more efficient product qualification.

Those skilled in the art will readily appreciate that the tubular body portion 52 of the access port 26 can be introduced into the abdominal cavity of a patient through the abdominal wall using an inserter or obturator. In this regard, as best seen in FIGS. 5 and 8 the end cap 76 on the proximal housing 50 includes diametrically opposed flanges 78a and 78b which are designed to cooperate with an obturator or introducer of the type described and illustrated in commonly assigned U.S. Pat. No. 9,545,264, the disclosure of which is herein incorporated by reference in its entirety. Other types of obturators or introducers could also be utilized for this purpose.

Single Lumen Gas Sealed Trocar Without Instrument Passage

Referring now to FIGS. 11 through 24, while the single lumen gas sealed access port 26 described above is adapted and configured to perform gaseous sealing for surgical instrumentation passing therethrough, stable cavity pressure and smoke evacuation of the surgical cavity, as well as being constructed to permit air entrainment and emergency relief of cavity pressure, it is also envisioned and well within the scope of the subject disclosure that an embodiment of the subject invention does not necessarily have to provide instrument access to the surgical cavity, but rather it can be configured as a single lumen gas sealed trocar without an instrument passage.

Figure 11:
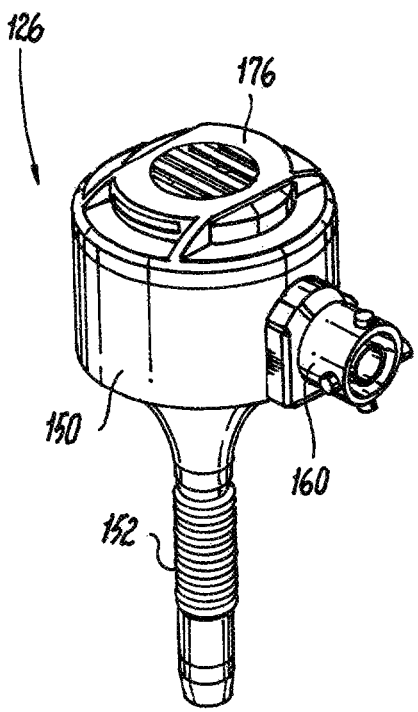
FIG. 11 is a perspective view of a single lumen gas sealed trocar constructed in accordance with a preferred embodiment of the subject invention which has a slotted or louvered end cap configured for air entrainment and emergency pressure relief, without permitting instrument access to the central bore of the cannula.
Figure 12:
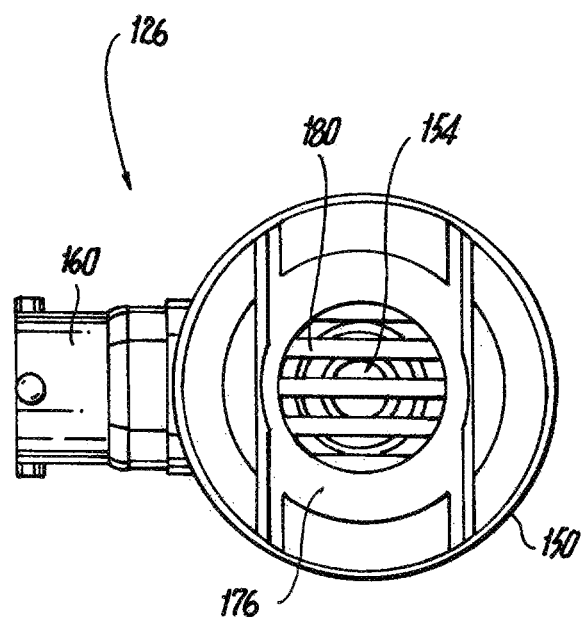
FIG. 12 is a top plan view of the single lumen gas sealed trocar shown in FIG. 11.

For example, there is illustrated in FIGS. 11 and 12, a gas sealed trocar 126 that is adapted and configured to maintain stable cavity pressure and effect smoke evacuation of a surgical cavity, as well as permit air entrainment and emergency pressure relief, by way of a concentric dual lumen manifold 160, but without permitting instrument access into and through the central cannula bore 154 of the body portion 152. In this regard, the central bore 154 of the gas sealed trocar 126 is covered by a louvered end cap 176 on housing portion 150 that includes a set of spaced apart slots 180, which physically prevent or otherwise block instrument access into and through the central bore 154 of the trocar 126.

Because surgical instruments are not inserted into this gas sealed trocar 126, the inside diameter (and therefore the outside diameter of the device) can be reduced significantly without sacrificing gaseous sealing functionality, as shown for example in FIGS. 16-17, described in more detail below. This can further increase the potential size-based advantages of the port of the subject invention. A gas sealed trocar of this type can have many alternative embodiments. For example, shown in FIGS. 18-20 and later described, the trocar device could include a thinner and/or flatter channel or an oblong channel, since the conduit does not have to be cylindrical in order to provide a gaseous seal around cylindrical surgical instruments. This design may allow for clinical advantages as the elliptical or oblong geometry of this embodiment aligns more closely with the linear skin incision made by the surgeon and therefore may provide for easier insertion and less trauma to the tissue surrounding the incision.

Figure 13:
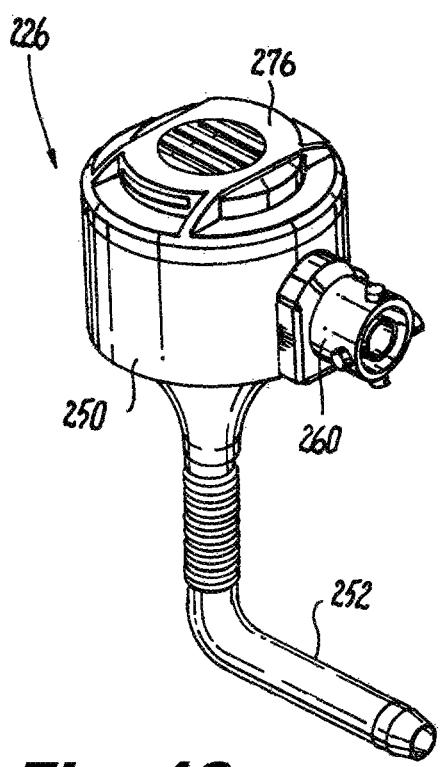
FIG. 13 is a perspective view of another embodiment of a single lumen gas sealed trocar as in FIG. 11, which has a non-linear tubular body portion.

The trocar device also does not have to include a straight or longitudinal pathway. For example, as shown in FIG. 13, a gas sealed trocar 226 with a proximal housing portion 250 having a louvered end cap 176 and bi-lumen manifold 260 could include a non-linear body portion 252 that is configured to bend 90 degrees from its axis. This construction allows for a number of improvements such as anchoring to a patient's abdominal wall during a laparoscopic surgical procedure, providing enhanced or user-directed smoke evacuation range and coverage, and eliminating clutter within the working space both inside and outside of the abdominal cavity.

Referring now to FIGS. 14-15, there is illustrated a gas sealed trocar 326 for performing an endoscopic surgical procedure in a surgical cavity of a patient, which includes a proximal housing portion 350 and an elongated single lumen tubular body portion 352 extending distally from the proximal housing portion 350 and defining a central cannula 354. The proximal housing portion 350 has an inlet path 356 for communicating with a pressurized gas line 30 of a tube set 20 and an outlet path 358 for communicating with a return gas line 32 of the tube set 20. The proximal housing portion 350 includes a manifold 360 defining the inlet path and the outlet path, wherein the inlet and outlet paths are arranged in parallel within the manifold 360. Alternatively, paths 356 and 358 could be formed in a manner that is integral with the proximal housing portion 350, without requiring a separate manifold.

The proximal housing portion 350 accommodates an annular jet assembly 364 for receiving pressurized gas from the inlet path 356 and for generating a gaseous sealing zone within the central cannula 354 of the tubular body portion 352 to maintain a stable pressure within the surgical cavity of the patient, wherein the proximal housing portion 350 is adapted and configured to permit air entrainment, but the body portion 352 is closed off to prevent access through the central cannula 354 into the surgical cavity, as described further below.

The proximal housing portion 350 includes a manifold 360 defining the inlet path and 356 the outlet path 358, wherein the inlet and outlet paths are arranged in parallel within the manifold 360. The proximal housing portion 350 also includes suture securement tangs 394 to facilitate securement of the device 326 during a surgical procedure. The proximal housing portion 350 further includes an end cap 376 with circumferentially disposed radial slots 377 to permit air entrainment and emergency relief of cavity pressure. The end cap 376 is also configured with a central aperture 378 to receive a plug 390 for closing the central cannula 354 of the tubular body portion 352, and thereby prevent air entrainment, if the need arises.

A distal end section of the tubular body portion 352 forms a closed conical tip 355 for facilitating percutaneous introduction of the device. Moreover, the closed distal tip 355 prevents the passage of a surgical instrument into the patient's body cavity through the central cannula 354. The distal end section of the tubular body portion 352 includes a plurality of apertures 392 for facilitating gas/fluid communication between the central cannula 354 of the tubular body portion 352 and the surgical cavity of the patient.

Figure 16:
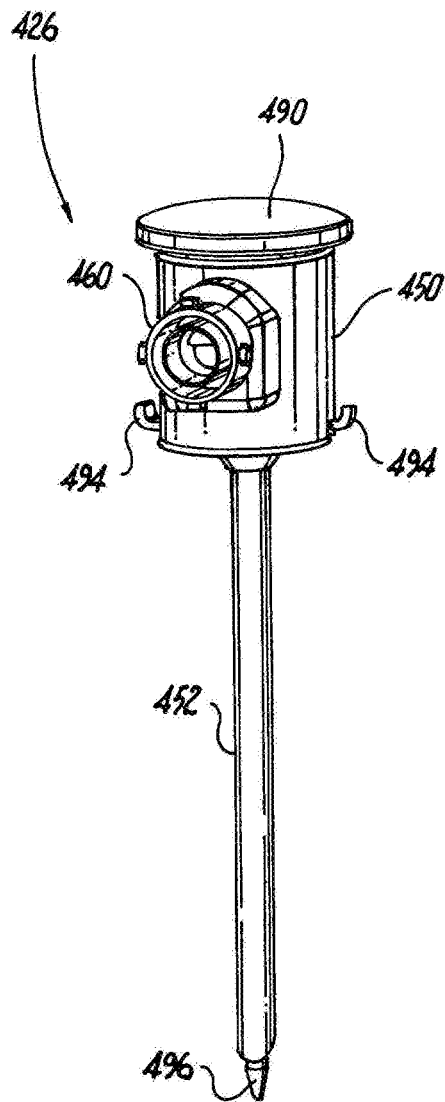
FIGS. 16 and 17 are perspective views of another embodiment of a single lumen gas sealed trocar constructed in accordance with the subject invention, wherein the trocar includes a tubular body portion with a central cannula or bore that is dimensioned to prevent instrument passage therethrough, while permitting access to an obturator.
Figure 17:
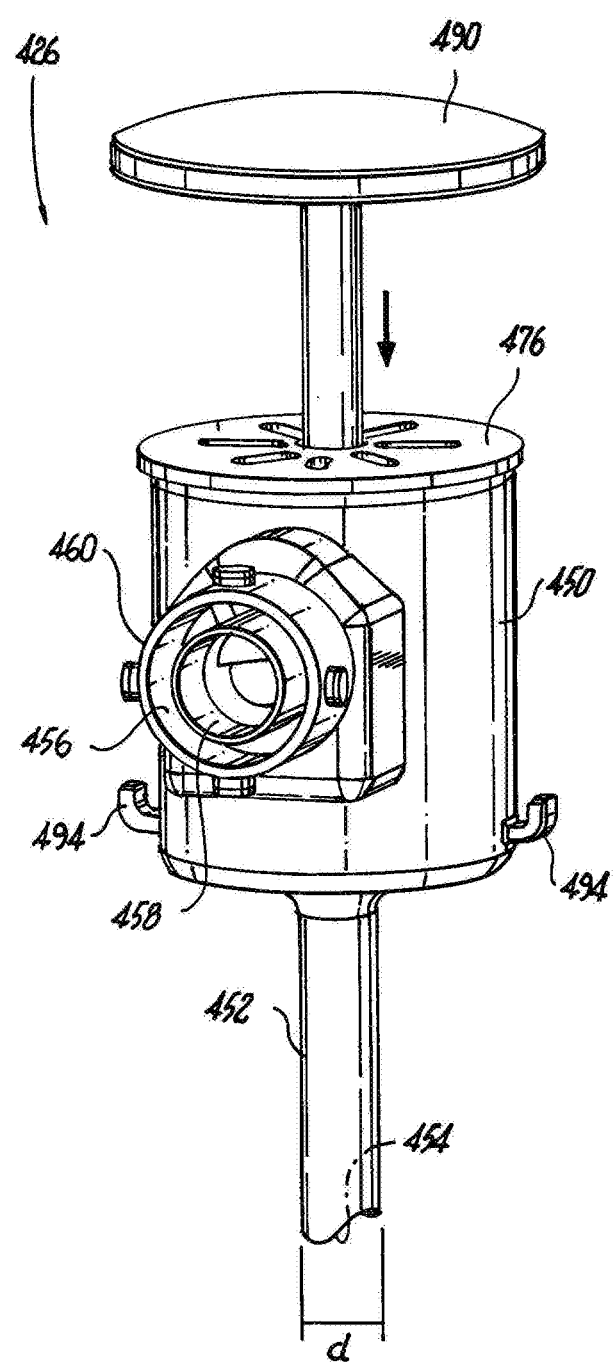

Referring now to FIGS. 16 and 17, there is illustrated a gas sealed trocar 426 for performing an endoscopic surgical procedure in a surgical cavity of a patient, which includes a proximal housing portion 450 and an elongated single lumen tubular body portion 452 extending distally from the proximal housing portion 450 and defining a central cannula 454.

The proximal housing portion 450 includes an end cap 476 that permits air entrainment and a dual lumen manifold 460 defining the inlet path 456 and the outlet path 458, wherein the inlet and outlet paths are arranged in a concentric manner within the manifold 460, rather than in a parallel manner as shown in FIG. 14. The proximal housing portion 450 further includes suture securement tangs 494.

In this embodiment, the tubular body portion 452, and more particularly the central bore or cannula 454 is dimensioned to prevent the passage of a surgical instrument therethrough. For example, the bore 454 could be dimensioned to prevent the introduction of a standard 5 mm endoscopic surgical device commonly used during laparoscopic surgery. Thus, the inner diameter "d" of bore 454 would be less than 5 mm. However, in such an instance, the obturator or introducer 490 would be dimensioned to pass through the central bore 454 to facilitate the percutaneous introduction of the trocar 426.

Figure 18:
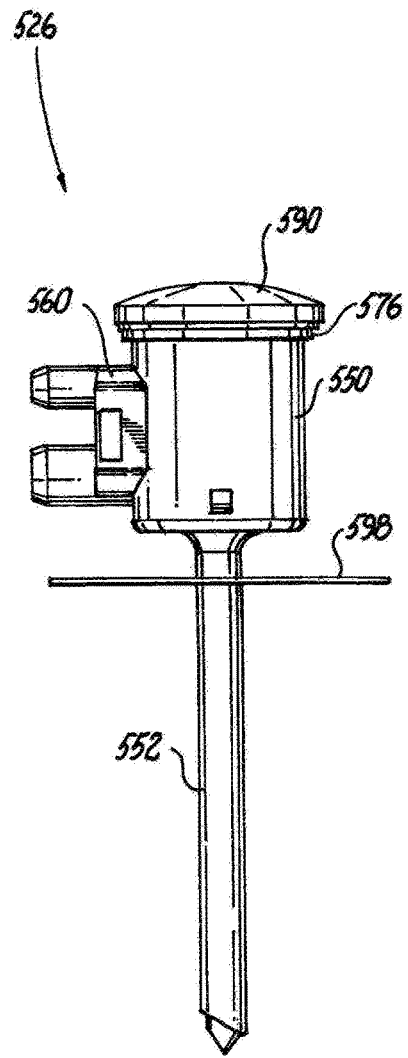
FIG. 18 is a side elevational view of another embodiment of a single lumen gas sealed trocar constructed in accordance with the subject invention, wherein the trocar includes a tubular body portion with an elliptical cross-section that is shaped to prevent instrument passage therethrough, while permitting access to an obturator, and also including an adhesive pad for retention purposes.
Figure 19:
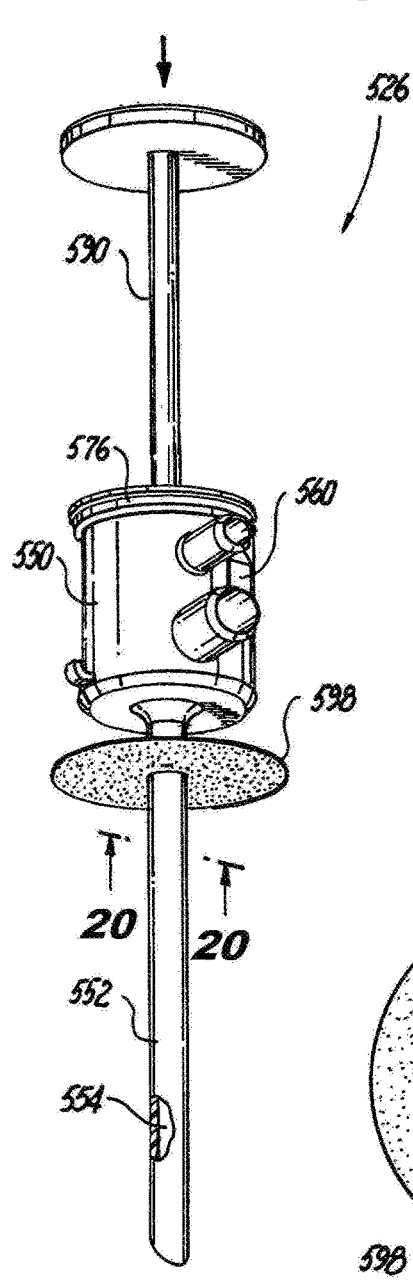
FIG. 19 is a perspective view of the single lumen gas sealed trocar shown in FIG. 18, during introduction of the obturator.
Figure 20:
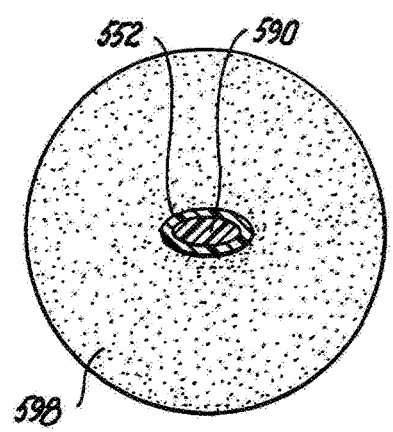
FIG. 20 is a cross-sectional view of the body portion of the trocar taken along line 20-20 of FIG. 19.

Referring now to FIGS. 18-20, there is illustrated a gas sealed trocar 526 for performing an endoscopic surgical procedure in a surgical cavity of a patient, which includes a proximal housing portion 550 and an elongated single lumen tubular body portion 552 extending distally from the proximal housing portion 550 and defining a central cannula 554. The proximal housing portion 550 includes a manifold 560, wherein the inlet and outlet paths are arranged in a parallel manner.

As best seen in FIG. 20, the tubular body portion 552 has a non-circular cross-sectional configuration. More particularly, as shown in FIG. 20, the tubular body portion 552 has an elliptical cross-sectional configuration. Also, an adhesive pad 598 is operatively associated with the tubular body portion 552 for retaining the trocar 500 in place during a surgical procedure.

Referring now to FIGS. 21-24, there is illustrated another embodiment of a single lumen gas sealed trocar constructed in accordance with the subject invention, which is designated generally by reference numeral 626. Gas sealed trocar 626 includes a proximal housing portion 650 and an elongated single lumen tubular body portion 652 extending distally from the proximal housing portion 650 and defining a central cannula 654. The proximal housing portion 650 includes a manifold 660, wherein the inlet and outlet paths are arranged in a parallel manner.

Figure 21:
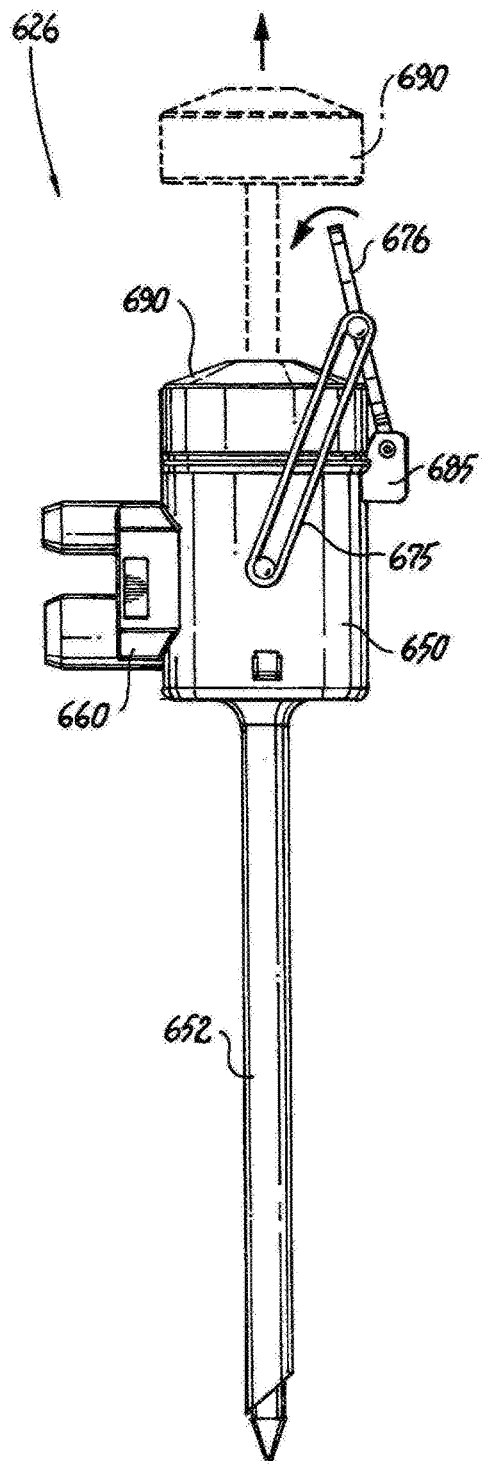
FIGS. 21-24 illustrate yet another embodiment of a single lumen gas sealed trocar constructed in accordance with the subject invention which is configured for air entrainment and emergency pressure relief, without permitting instrument access to the central bore of the cannula, wherein the trocar includes a mechanically actuated slotted or louvered end cap that is mounted to move into a closed and locked position when an obturator is removed from the device.
Figure 22:
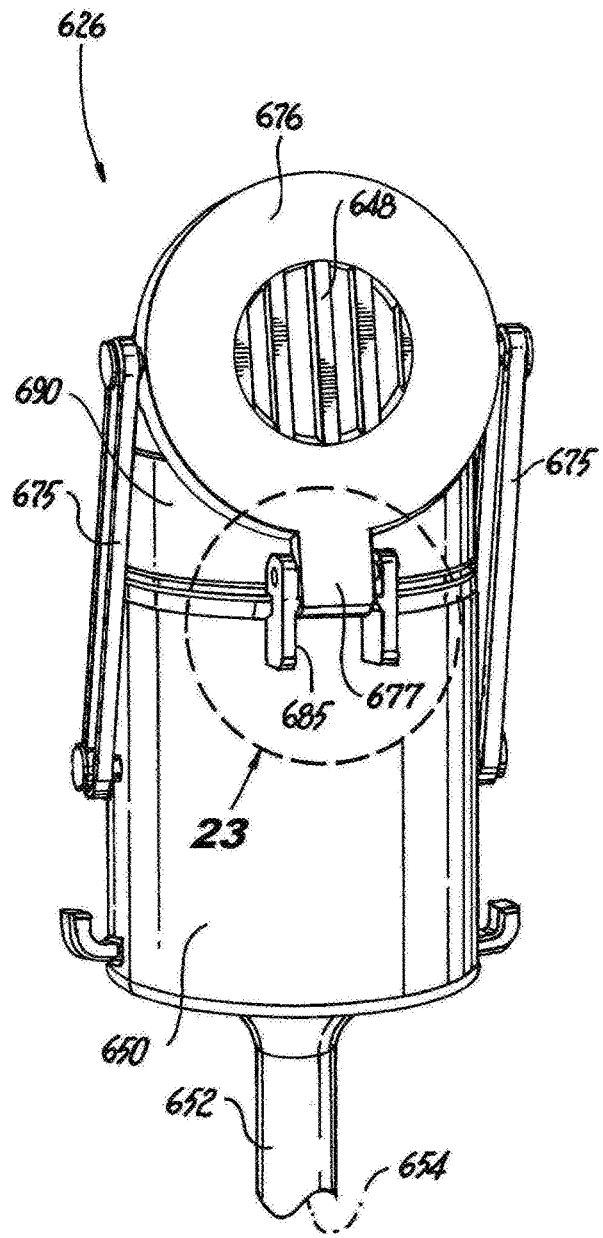
Figure 23:
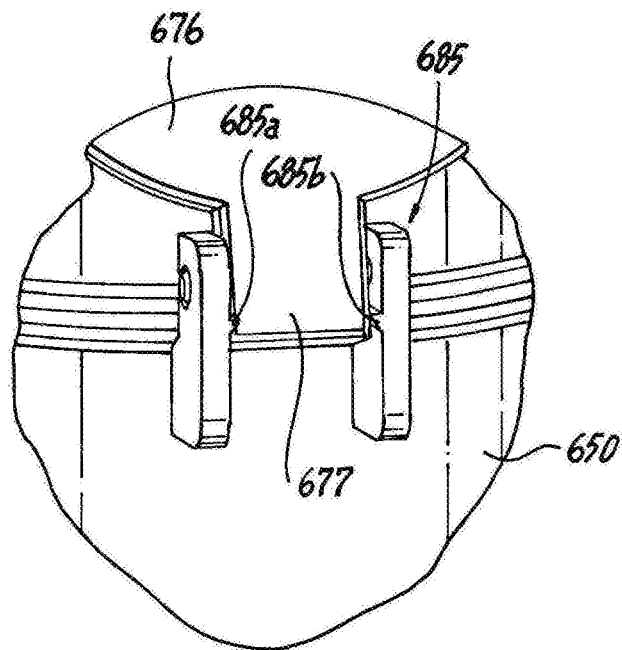
Figure 24:
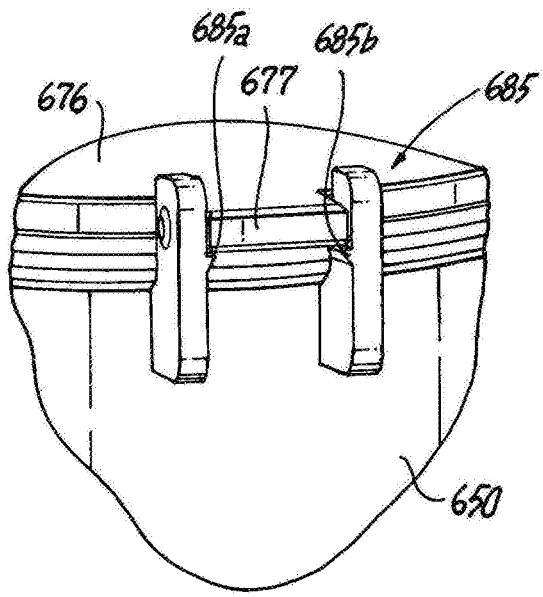

The proximal housing portion 650 further includes a hinged end cap 676 that is mechanically actuated and mounted to move from an open position shown in FIGS. 21-23 to a closed position shown in FIG. 24 upon the removal of an obturator 690 from the trocar 600 to prevent access to the central cannula 654. More particularly, the proximal housing portion 650 and the hinged end cap 676 are operatively connected to one another by biasing bands 675 that bias the end cap 676 into a normally closed position.

The end cap 676 has louvers or spaced apart slots 648 that permit air entrainment into the central cannula 654 and emergency relief of cavity pressure without permitting instrument access into and through the central cannula 654 of the tubular body portion 652. In addition, a locking mechanism 685 is provided on the proximal housing portion 650 for retaining the hinged end cap 676 is the closed position, as best seen in FIG. 24. More particularly, the locking mechanism 685 includes a pair of locking tabs 685*a* and 685*b* for capturing and retaining the flange 677 of the end cap 676.

Separable Two-Part Single Lumen Gas Sealed Access Port for Robotic Surgery

Referring to FIGS. 25 through 30, there is illustrated another embodiment of the gas circulation system of the subject invention which is designated generally by reference numeral 710, and which is configured for use in robotically assisted minimally invasive surgical procedures. More particularly, the gas circulation system 710 is adapted for use in conjunction with a Da Vinci Xi type robotic system that is manufactured and sold by Intuitive Surgical, Inc.

Figure 25:
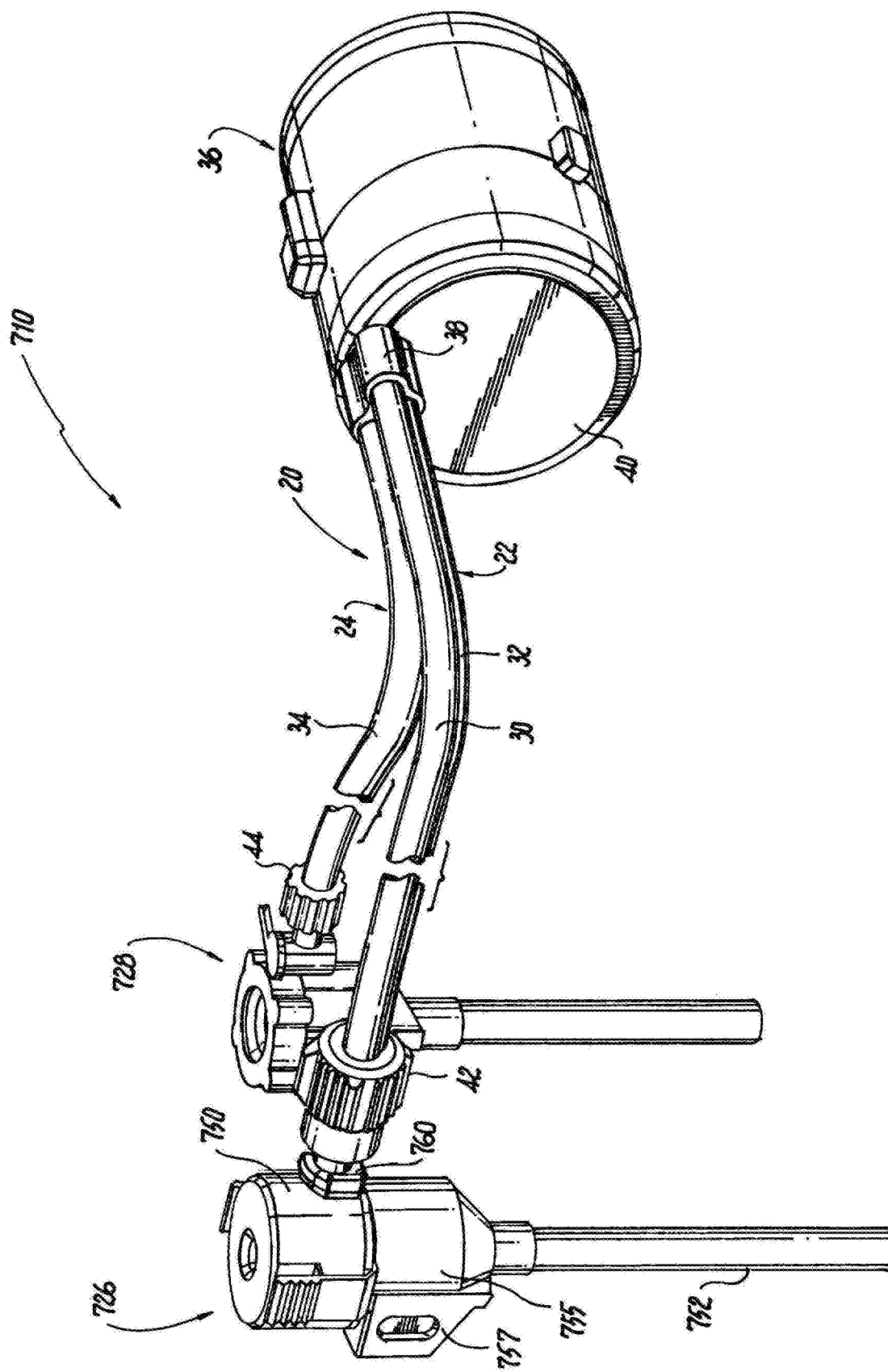
FIG. 25 is a perspective view of a gas circulation system constructed in accordance with the subject invention that is adapted and configured for use during a robotically assisted surgical procedures, which includes a multi-lumen filtered tube set, a two-part single lumen gas sealed access port with a detachable housing portion and a two-part single lumen valve sealed access port with a detachable housing portion.

Referring to FIG. 25, the gas circulation system 710 includes a multi-lumen tube set 20 having a dual lumen portion 22, a single lumen portion 24 and a multi-path filter cartridge assembly 36. The dual lumen portion 22 is adapted and configured to communicate with a separable two-part single lumen gas sealed access port designated generally by reference numeral 726. The single lumen portion 24 is adapted and configured to communicate with a separable two-part single lumen valve sealed access port designated generally by reference numeral 728.

Figure 26:
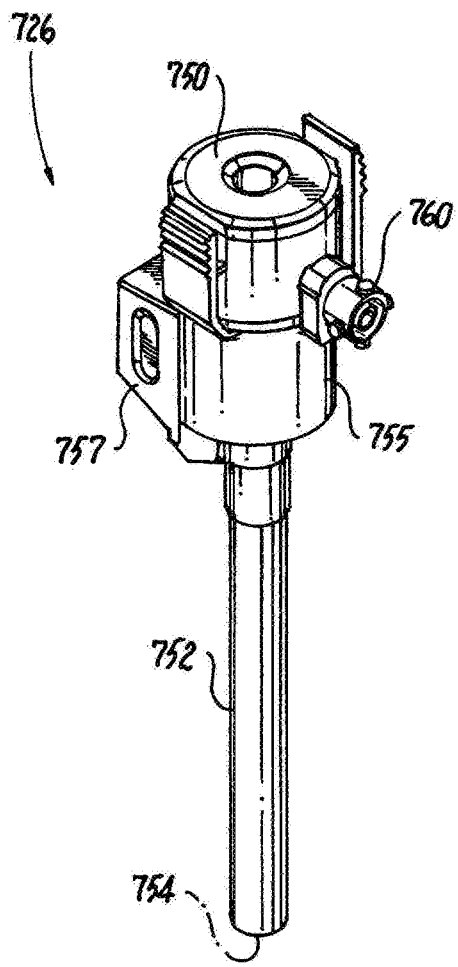
FIG. 26 is a perspective view of the single lumen gas sealed access port shown in FIG. 25, which includes a reusable distal cannula portion configured for robotic manipulation and a detachable housing portion configured for gaseous sealing, gas recirculation and smoke evacuation.

Referring to FIG. 26, the gas sealed access port 726 is particularly configured for use in robotic surgery. It includes a proximal housing portion 750 that is adapted to be selectively coupled with a separate tubular body portion 752, as described in more detail below. The tubular body portion 752 is configured for manipulation by a robotic surgical system. More particularly, the proximal reception portion 755 of the tubular body portion 752 includes a radially outwardly extending grasping flange 757 for enabling a Da Vinci Xi type robotic manipulator (not shown) to grasp and move the abdominal port 750 during a minimally invasive surgical procedure.

With reference to FIGS. 27-30, the proximal housing portion 750 of the gas sealed access port 726 includes a lower housing portion 751 dimensioned and configured to be accommodated within the upper reception portion 755 of the tubular body portion 752. An O-ring 759 is provided within the upper reception portion 755 to seal against the exterior of lower housing portion 751. A tubular stem 753 extends through and from the lower housing portion 751 to communicate directly with the tubular bore or cannula 754 of the tubular body portion 752, when the two structures are attached together for use.

Figure 30:
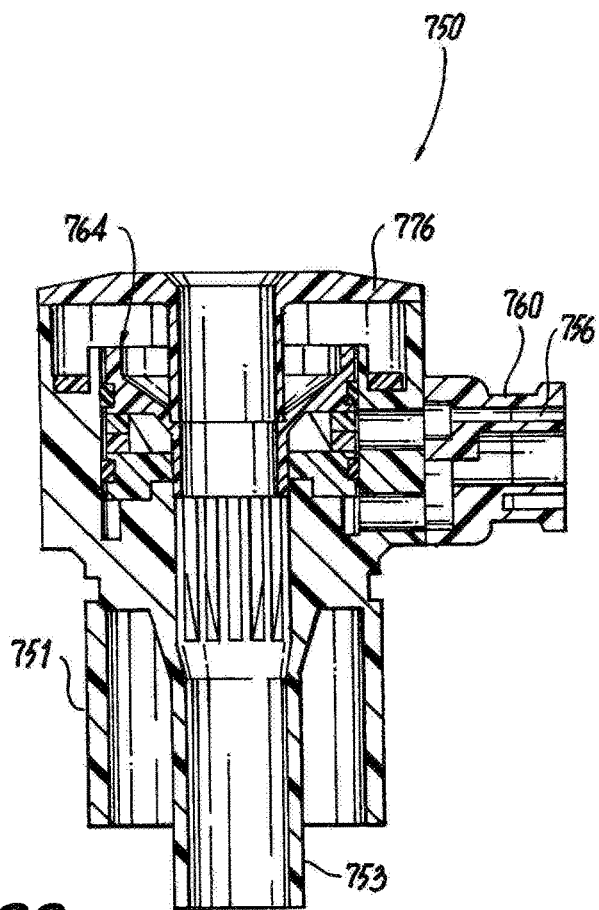
FIG. 30 is a cross-sectional view of the separable housing portion of the single lumen gas sealed access port taken along line 30-30 of FIG. 28.

Referring to FIG. 30, the proximal housing portion 750 further includes an interior chamber to accommodate an annular jet assembly 764. The annular jet assembly 764 is configured to receive pressurized gas from the inlet path 756 and generate a gaseous or pneumatic sealing zone within the tubular stem 753. Because the tubular stem 753 is in pneumatic communication with the central cannula bore 754 of the tubular body portion 752, the device can maintain a stable cavity pressure and provide smoke evacuation.

Figure 27:
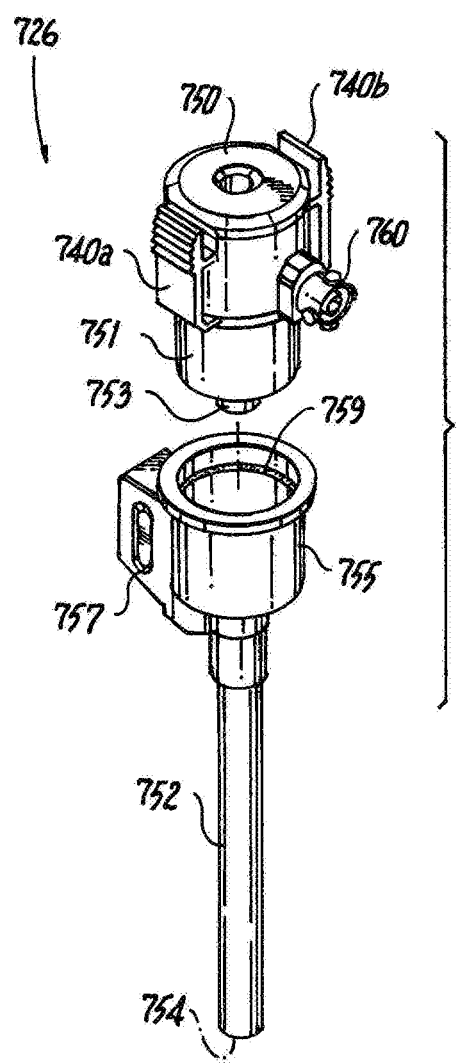
FIG. 27 is an exploded perspective view of the single lumen gas sealed access port of FIG. 26, with the housing portion separated from the reusable cannula or tubular body portion for ease of illustration.
Figure 27A:
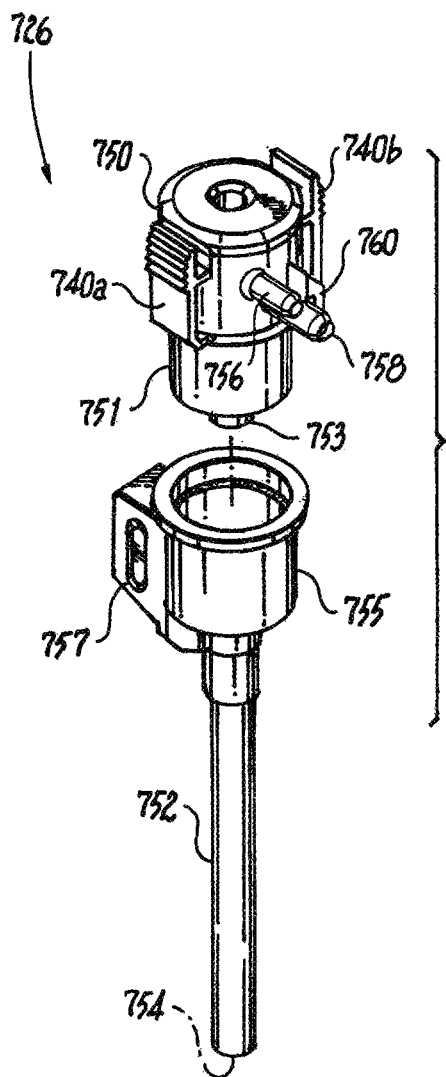
FIG. 27A is an exploded perspective view of an alternative version of the single lumen gas sealed access port of FIG. 26, wherein the manifold includes parallel connectors as opposed to a concentric connector.
Figure 28:
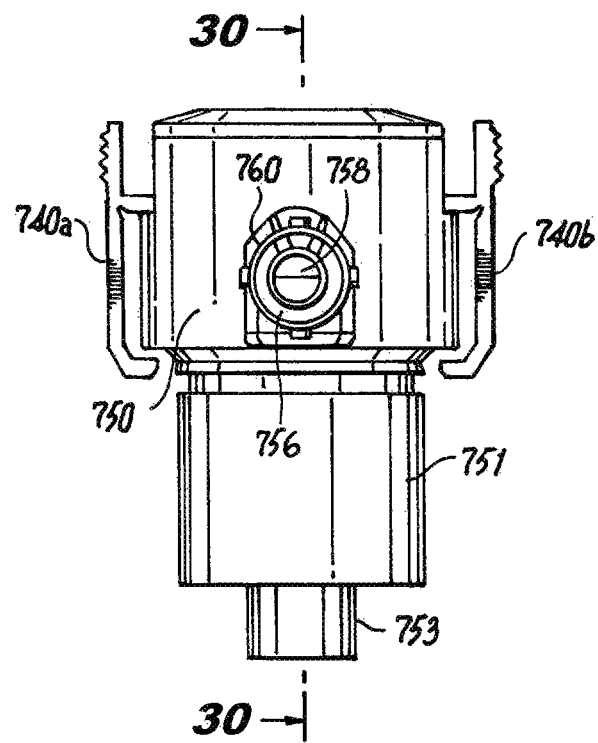
FIG. 28 is a side elevational view of the separable housing portion of the single lumen gas sealed access port of FIG. 26.
Figure 29:
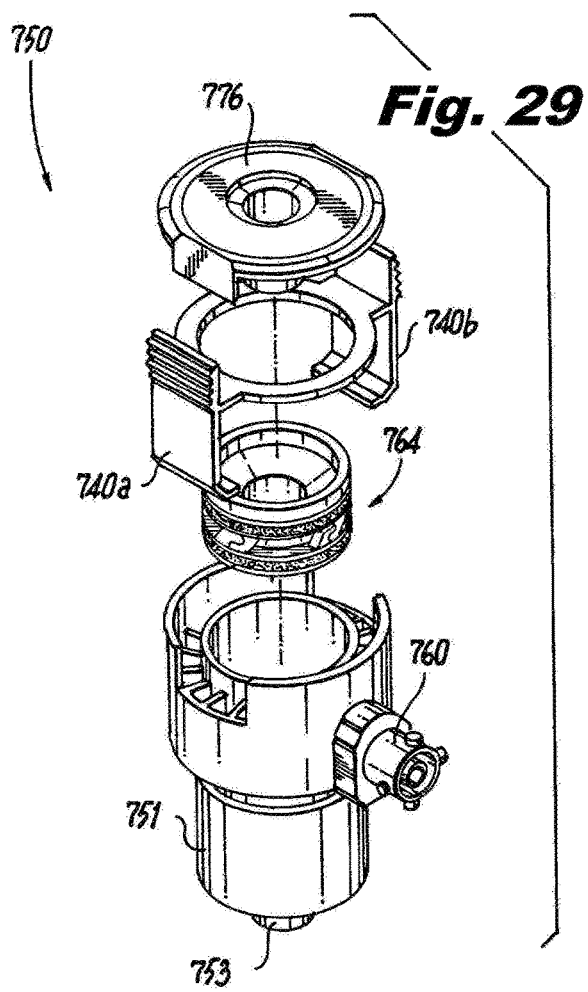
FIG. 29 is an exploded perspective view of the separable housing portion of the single lumen gas sealed access port of FIG. 26, with the component parts thereof separated for ease of illustration.

With reference to FIGS. 27 and 29, the proximal housing portion 750 of access port 726 is configured to be selectively or otherwise detachably coupled to the tubular body portion 752 by a pair of diametrically opposed spring-loaded locking tabs 740*a* and 740*b*. As best seen in FIG. 28, the separable housing portion 750 also includes a dual lumen manifold 760 to manage the flow of the pressure and return lines through concentric paths 756, 758. Alternatively, as shown in FIG. 27A, the manifold 760 could include parallel inlet and outlet paths 756 and 758.

Separable Two-Part Single Lumen Gas Sealed Access Port for Endoscopic Surgery

Referring now to FIGS. 31 through 34, there is illustrated another embodiment of the gas circulation system of the subject invention which is designated generally by reference numeral 810, which is adapted and configured for use in endoscopic surgical procedures. The system 810 includes a multi-lumen tube set 20 having a dual lumen portion 22, a single lumen portion 24 and a multi-path filter cartridge assembly 36.

Figure 31:
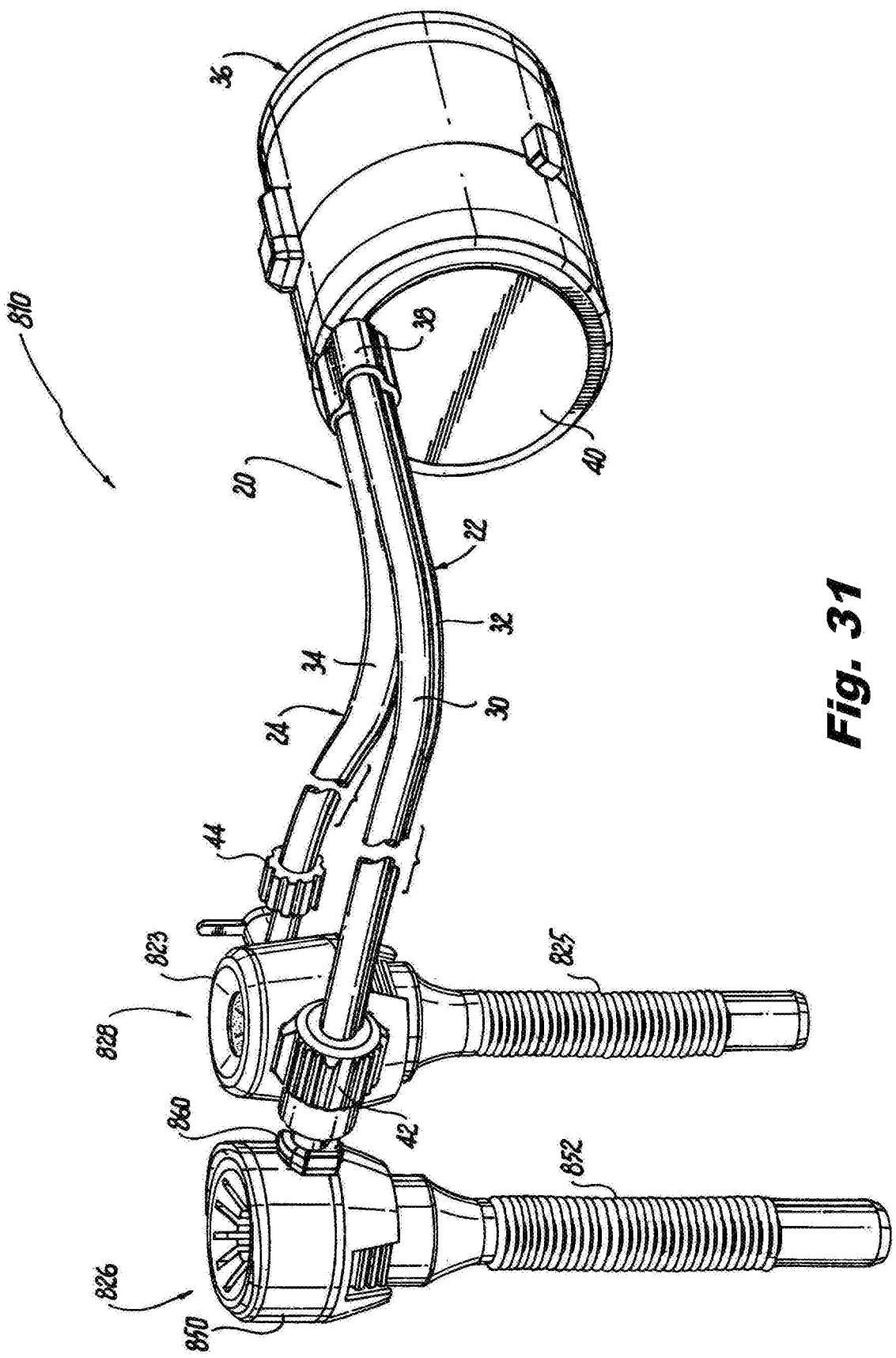
FIG. 31 is a perspective view of a gas circulation system constructed in accordance with the subject invention that is adapted and configured for use during an endoscopic or laparoscopic surgical procedure, which includes a multi-lumen filtered tube set, a single lumen gas sealed access port with a detachable housing portion and a single lumen valve sealed access port with a detachable housing portion.

Referring to FIG. 31, the dual lumen portion 22 of tube set 20 is adapted and configured to communicate with a two-part single lumen gas sealed access port designated generally by reference numeral 826, which includes a proximal housing portion 850 and a separable tubular body portion 852. The single lumen portion 24 of tube set 20 is adapted and configured to communicate with a two-part single lumen valve sealed access port designated generally by reference numeral 828, which includes a proximal housing portion 823 and a separable tubular body portion 825. Those skilled in the art will readily appreciate that the single lumen portion 24 of tube set 20 can be connected to a one-piece valve sealed access port, without departing from the spirit or scope of the subject invention.

Figure 32:
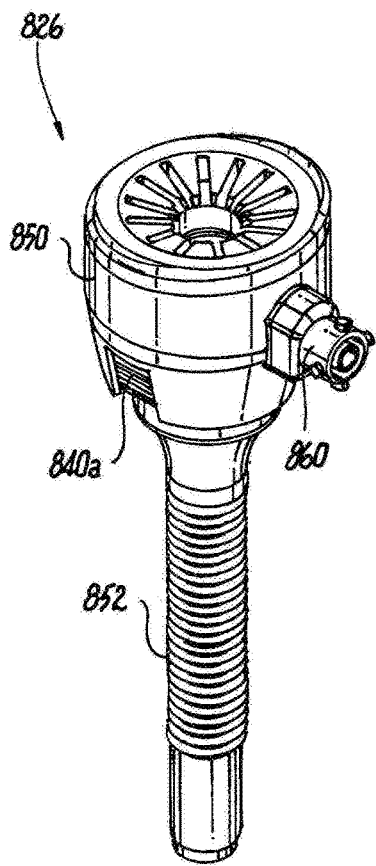
FIG. 32 is a perspective view of the single lumen gas sealed access port shown in FIG. 31, which includes a distal cannula portion and a detachable housing portion configured for gaseous sealing, gas recirculation and smoke evacuation.
Figure 33:
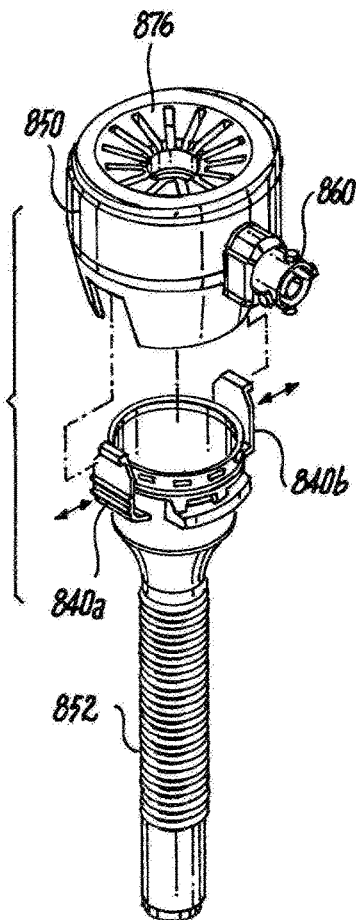
FIG. 33 is an exploded perspective view of the single lumen gas sealed access port of FIG. 32, with the housing portion separated from the tubular body portion for ease of illustration.
Figure 34:
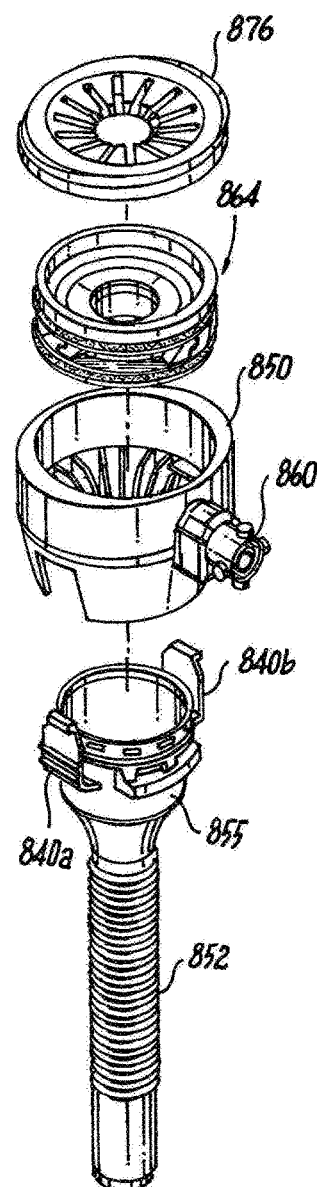
FIG. 34 is an exploded perspective view of the separable housing portion of the single lumen gas sealed access port of FIG. 32, with the component parts thereof separated for ease of illustration.

Referring to FIGS. 32 and 33, the gas sealed access port 826 includes a proximal housing portion 850 that is adapted to be selectively coupled with the upper reception portion 855 of tubular body portion 852. More particularly, the proximal housing portion 850 of the access port 826 is configured to be selectively coupled to the upper reception portion 855 of tubular body portion 852 by a pair of diametrically opposed spring-loaded locking tabs 840*a* and 840*b* operatively associated with the upper reception portion 855.

The separable housing portion 850 includes an end cap 876 and a dual lumen manifold 860 to manage the flow of the pressure and return lines. Housing portion 850 also has an interior chamber that accommodates an annular jet assembly 864 configured to generate a gaseous or pneumatic sealing zone within the central cannula bore of the separable tubular body portion 852, to maintain a stable cavity pressure and provide smoke evacuation.

Method of Deploying a Single Lumen Two-Part Gas Sealed Access Port

Figure 35:
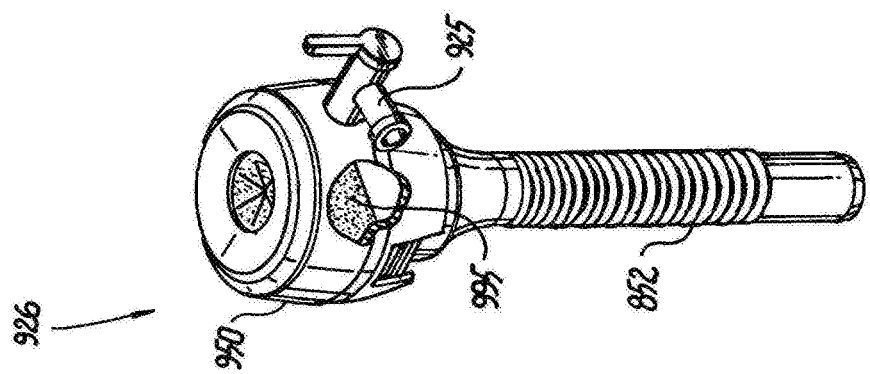

Referring to FIGS. 35-38, the subject invention is also directed to a novel method of retrofitting a separable two-part valve sealed surgical access port to perform an endoscopic surgical procedure in a surgical cavity of a patient. As shown in FIG. 35, the method first includes the step of obtaining a separable two-part surgical access port 926 having a valve sealed proximal housing portion 950 that is detachably engaged to a single lumen tubular body portion 852. The proximal housing portion 950 includes a mechanical duckbill valve 995 and a conventional luer type fitting 925.

Figure 38:
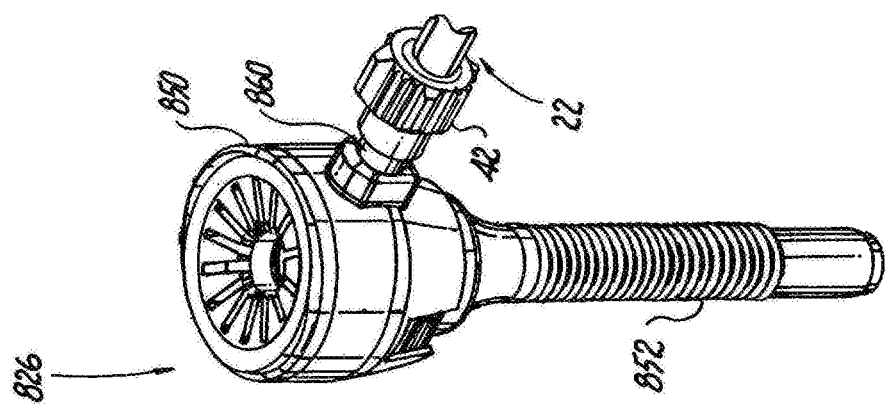
Figure 37:
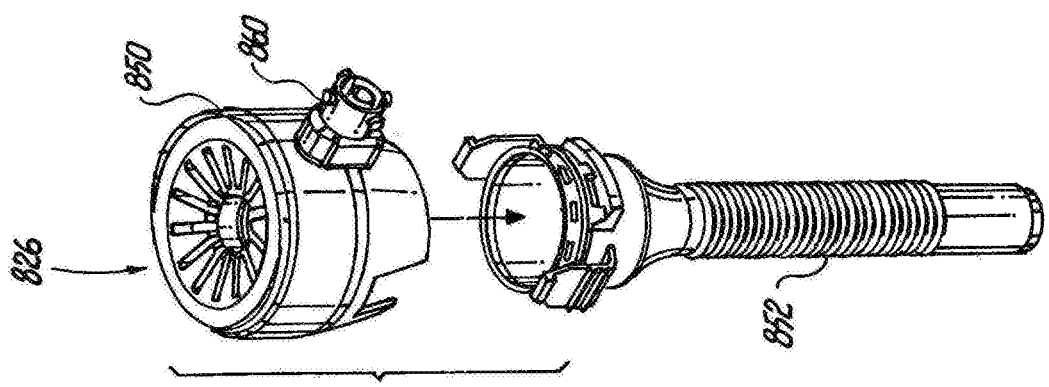
Figure 36:
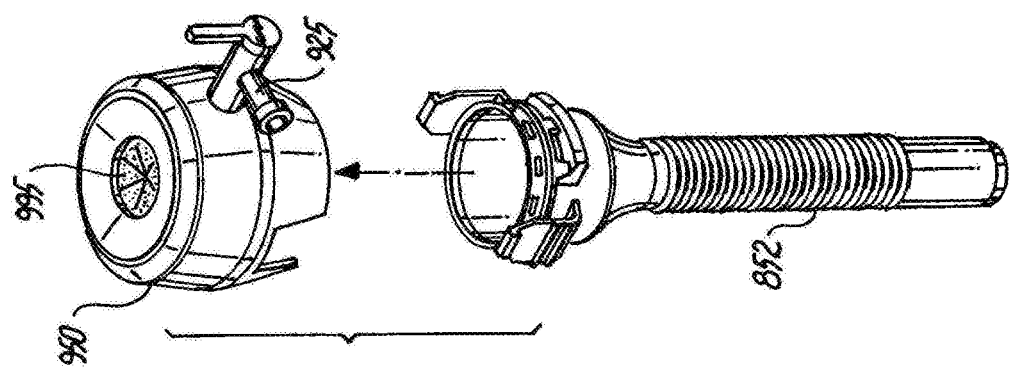

The method further includes the steps of detaching the valve sealed proximal housing portion 950 from the single lumen tubular body portion 852, as shown in FIG. 36, and then selectively attaching a gas sealed proximal housing portion 850 with manifold 860 to the single lumen tubular body portion 852, as shown in FIG. 37. Then, as shown in FIG. 38, the method further includes the step of connecting the gas sealed proximal housing portion 850 of the assembled port 826 to a source of pressurized gas for generating a gaseous sealing zone within a central cannula of the single lumen tubular body portion 852 to maintain a stable pressure within the surgical cavity of a patient.

While the gas circulation system, multi-lumen tube set and gas sealed access ports and trocars of the subject disclosure has been shown and described with reference to preferred embodiments, those skilled in the art will readily appreciate that changes and/or modifications may be made thereto without departing from the scope of the subject disclosure.

What is claimed is:

1. A surgical access port for performing an endoscopic surgical procedure in a surgical cavity of a patient, comprising:
a proximal housing portion defining an interior chamber and an elongated single lumen tubular body portion extending distally from the proximal housing portion, the tubular body portion defining a central lumen without a surrounding annular lumen, the proximal housing portion having a manifold that only includes an inlet path for communicating with a pressurized gas line of a tube set and an outlet path for communicating with a return gas line of the tube set, and wherein the manifold is without a flow path for communicating with a source of insufflation gas or for communicating with a pressure sensor, the proximal housing portion accommodating an annular jet assembly within the interior chamber thereof for receiving a flow of pressurized gas from the inlet path and for generating a gaseous sealing zone within the central lumen of the tubular body portion using the pressurized gas to maintain a stable pressure within the surgical cavity of the patient and to provide gas sealed instrument access to the surgical cavity of the patient through the central lumen, wherein the surgical access port is incapable of delivering insufflation gas to the surgical cavity of the patient or sensing cavity pressure within the surgical cavity of the patient, because the central lumen of the tubular body portion is without a surrounding annular lumen to do so and because the manifold of the proximal housing is without a flow path for communicating with a source of insufflation gas or for communicating with a pressure sensor.

2. A surgical access port as recited in claim 1, which is adapted and configured to perform smoke evacuation from the surgical cavity of the patient in conjunction with another access port.

3. A surgical access port as recited in claim 1, which is adapted and configured to permit air entrainment into the central lumen of the tubular body portion.

4. A surgical access port as recited in claim 1, wherein the inlet and outlet paths are concentrically arranged within the manifold.

5. A surgical access port as recited in claim 1, wherein the inlet and outlet paths are arranged in parallel within the manifold.

6. A surgical access port as recited in claim 1, wherein gas from the gaseous sealing zone is directed to the outlet path of the manifold of the proximal housing portion.

* * * * *